United States Patent [19]

Ohta et al.

[11] Patent Number: 4,959,092
[45] Date of Patent: Sep. 25, 1990

[54] SUBSTITUTED PHENYL (OR PYRIDYL) UREA COMPOUND AND HERBICIDAL COMPOSITION CONTAINING THE SAME AS ACTIVE INGREDIENT

[75] Inventors: Hiroki Ohta, Kokubunji; Katsutoshi Sato, Machida; Susumu Matsumoto, Yokohama; Kazuo Ishii; Yumiko Miura, both of Tokyo; Hisao Watanabe, Yokohama; Seiichi Suzuki; Yoichiro Umeki, both of Tokyo; Hiroshi Hanabe, Yokohama, all of Japan

[73] Assignee: Mitsubishi Kasei Corporation, Tokyo, Japan

[21] Appl. No.: 198,287

[22] Filed: May 25, 1988

[30] Foreign Application Priority Data

Jun. 3, 1987 [JP] Japan ................... 62-139399
Dec. 11, 1987 [JP] Japan ................... 62-313718
Dec. 11, 1987 [JP] Japan ................... 62-313720
Dec. 14, 1987 [JP] Japan ................... 62-315858
Dec. 14, 1987 [JP] Japan ................... 63-315860

[51] Int. Cl.$^5$ .................. C07D 307/79; A01N 43/12
[52] U.S. Cl. ........................... 71/88; 71/94; 546/268; 549/398; 549/462
[58] Field of Search ............... 546/268; 549/398, 462; 71/94, 88

[56] References Cited

U.S. PATENT DOCUMENTS

| 3,060,235 | 10/1962 | Martin et al. | 564/49 |
| 3,119,682 | 1/1964 | Martin et al. | 71/98 |
| 4,123,256 | 10/1978 | Yoshida et al. | 71/105 |
| 4,129,436 | 12/1978 | Takemoto et al. | 71/120 |
| 4,334,912 | 6/1982 | Yoshida et al. | 71/94 |
| 4,426,385 | 6/1984 | Cain | 514/594 |
| 4,838,924 | 6/1989 | Takematsu et al. | 71/88 |

FOREIGN PATENT DOCUMENTS 8700840 2/1987 PCT Int'l Appl.

*Primary Examiner*—John M. Ford
*Assistant Examiner*—Catherine Scalzo
*Attorney, Agent, or Firm*—Oblon, Spivak, McClelland, Maier & Neustadt

[57] ABSTRACT

The present invention relates to a substituted phenyl(or pyridyl)urea compound and a herbicidal composition containing the substituted phenyl(or pyridyl)urea compound as an active ingredient.

The compound has the formula:

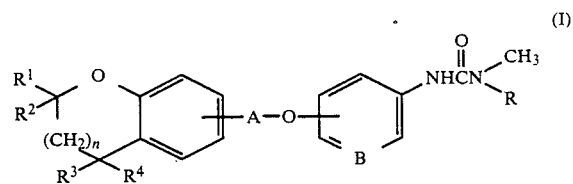

wherein
A represents an alkylene group; B represents a nitrogen atom or CH; R represents a hydrogen atom, a lower alkyl group or a lower alkoxy group;
$R^1$, $R^2$, $R^3$ and $R^4$ independently represent a hydrogen atom or a methyl group; and n is 0 or 1.

27 Claims, No Drawings

SUBSTITUTED PHENYL (OR PYRIDYL) UREA COMPOUND AND HERBICIDAL COMPOSITION CONTAINING THE SAME AS ACTIVE INGREDIENT

BACKGROUND OF THE INVENTION

The present invention relates to a substituted phenyl(or pyridyl)urea compound and a herbicidal composition containing the substituted phenyl(or pyridyl)urea compound as an active ingredient.

More particularly, the present invention relates to a compound represented by the following general formula (I):

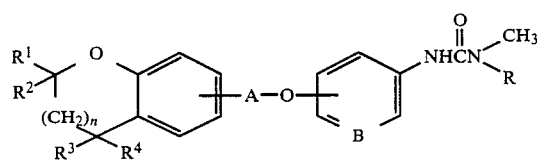

wherein A represents an alkylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1, and a herbicidal composition comprising as an active ingredient a herbicidally effective amount of compound represented by the following general formula:

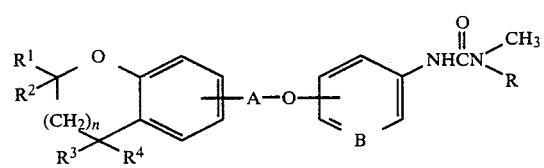

wherein A represents an alkylene group; B represents a nitrogen atom or CH; R represents a hydrogen atom, a lower alkyl group or a lower alkoxy group; $R^1$, $R^2$, $R^3$ and $R^4$ independently represent a hydrogen atom or a methyl group; and n is 0 or 1, and
a herbicidally acceptable carrier or adjuvant.

It has already been known that a phenoxyphenylurea derivative has a herbicidal activity (Belgian Pat. No. 593743), and that a benzyloxyphenylurea derivative has a herbicidal activity (Japanese Patent Application Laid-Open (KOKAI) No. 53-44544 (1978)). It is also known that a phenethyloxyphenylurea derivative has a herbicidal activity (Japanese Patent Application Laid-Open (KOKAI) No. 53-108947 (1978)), and that a benzyloxypyridylurea and a phenethyloxypyridylurea derivative have a herbicidal activity (Japanese Patent Application Laid-Open (KOKAI) No. 55-122764 (1980)). Furthermore, it is known that a benzopyranyloxyphenylurea derivative has a herbicidal activity (PCT Patent Application Laid-Open No. WO87/00840). These compounds, however, are insufficient in the selectivity to crops or the strength of the herbicidal activity. Chemical substances (compounds) are very often changed in the presence or absence of the herbicidal activity, or the strength of the herbicidal activity, or in the selectivity of the herbicidal function by slightly changing the structure thereof. It is, therefore, difficult to forecast in advance the herbicidal activity or the selectivity of a new compound merely from the similarity of a chemical structure.

On the other hand, Japanese Patent Application Laid-Open (KOKAI) No. 57-158753 (1982) discloses compounds containing in the chemical structure a benzofuranyloxyphenylurea component as a bicyclooxyphenylurea having an insecticidal activity. These are, however, compounds having an insecticidal activity and no relationship to the above-described urea derivatives having a herbicidal activity is disclosed in Japanese Patent Application Laid-Open (KOKAI) No 57-158753 (1982).

Accordingly, the development of a substituted phenyl(or pyridyl)urea derivative exhibiting a high herbicidal effect in upland field and paddy field and having an excellent selectivity so as to do no practical harm to the crops has been in strong demand.

As a result of studies of the present inventors it has been found that a compound represented by the following general formula (I):

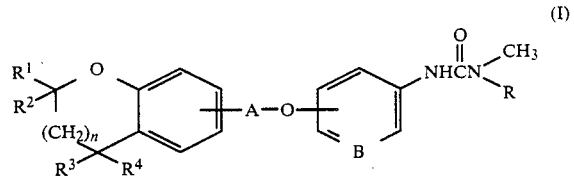

wherein A represents an alkylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1, is capable of controlling weeds in upland fields, such as lambsquarters (*Chenopodium album*), goosefoot (*Chenopodium album* var. *centrorubrum*), persicaria blumei gross (*Polygonum blumei*), ladysthumb (*Polygonum persicaria*), livid amaranth (*Amaranthus lividus*), common purselane (*Portulaca oleracea*), common chickweed (*Stellaria media*), deadnettle (*Lamium amplexicaule*), large crabgrass (*Digitaria sanguinalis*), goosegrass (*Eleusine indica*), green foxtail (*Setaria viridis*), water foxtail (*Alopecurus aequalis*) and flat-sedge (*Cyperus microiria*) and weeds in paddy fields, such as false pimpernel (*Lindernia procumbens*), toothcup (*Rotala indica*), abunome (*Dopatrium junceum*), american waterwort (*Elatine triandra*), narrowleaf waterplantain (*Alisma canaliculatum*), barnyardgrass (Echinochloa crus-*galli* L. Beauv. var. *crus-galli*), umbrella plant (*Cyperus difformis*) and duck-tongue weed (*Monochloria vaginalis*) by the preemergence treatment or by the treatment during the growing stage, and in addition, do no practical harm to crop plants such as rice (*Oryza sative*), sunflower (*Helianthus annuus*), potato (*Salanum tuberosum*), wheat (*Triticum aestivum*), barley (*Hordeum vulgare*), sugar cane (*Saccharum officinarum*), and corn (*Zea mays*). On the basis of this finding, the present invention has been attained.

SUMMARY OF THE INVENTION

In a first aspect of the present invention there is provided a compound represented by the following general formula (I):

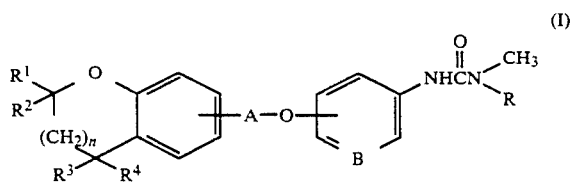

wherein A represents an alkylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1.

In a second aspect of the present invention, there is provided a herbicidal composition comprising as an active ingredient a herbicidally effective amount of compound represented by the following general formula:

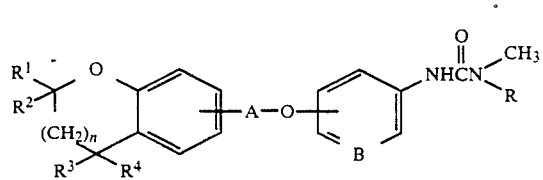

wherein A represents an alkylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1, and a herbicidally acceptable carrier or adjuvant.

In a third aspect of the present invention, there is provided a method of controlling the growth of weeds, which method comprises applying a herbicidally effective amount of compound represented by the following general formula:

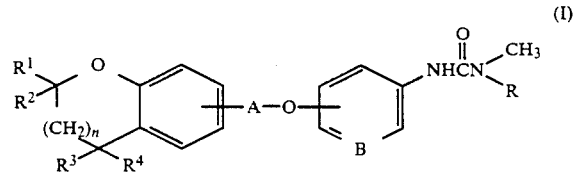

wherein A represents an alkylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1.

DESCRIPTION OF THE PREFERRED EMBODIMENTS:

A substituted phenyl(or pyridyl)urea compound according to the present invention is a novel compound represented by the following general formula (I)

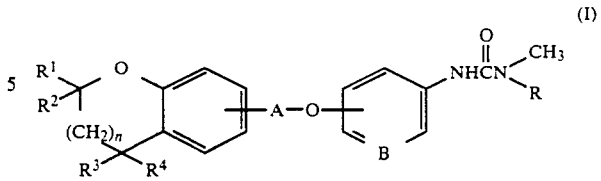

wherein A represents an alkylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1.

As compounds represented by the general formula (I), the following novel compounds represented by the general formula (II) to (V), respectively, may be exemplified.

(1) An N'-aryl-N-methylurea derivative represented by the following general formula (II):

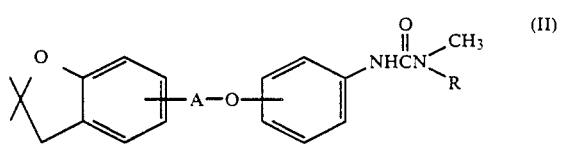

wherein A represents an alkylene group; and R represents a hydrogen atom, a lower alkyl group or a lower alkoxy group.

(2) An N'-phenyl-N-methylurea derivative represented by the following general formula (III):

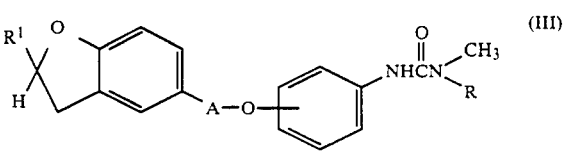

wherein A represents an alkylene group; R represents a hydrogen atom, a lower alkyl group or a lower alkoxy group; and $R^1$ represents a hydrogen atom or a methyl group.

(3) An N'-(5-pyridyl)-N-methylurea derivative represented by the following general formula (IV):

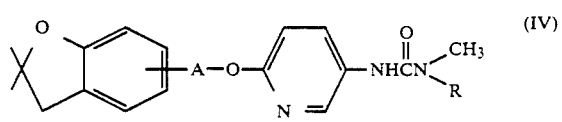

wherein A represents an alkylene group; and R represents a hydrogen atom, a lower alkyl group or a lower alkoxy group.

(4) An N'-phenyl-N-methylurea derivative represented by the following general formula (V):

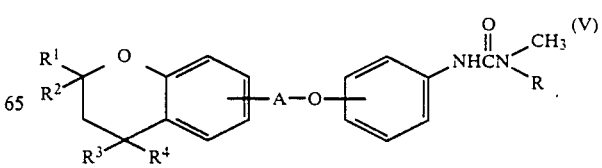

wherein A represents an alkylene group; R represents a hydrogen atom, a lower alkyl group or a lower alkoxy group; and $R^1$, $R^2$, $R^3$ and $R^4$ independently represent a hydrogen atom or a methyl group.

In the general formula (I), A represents an alkylene group having 1 to 6 carbon atoms, preferably 1 to 3 carbon atoms. As an alkylene group, straight-chain or branched alkylene group such as, for example,

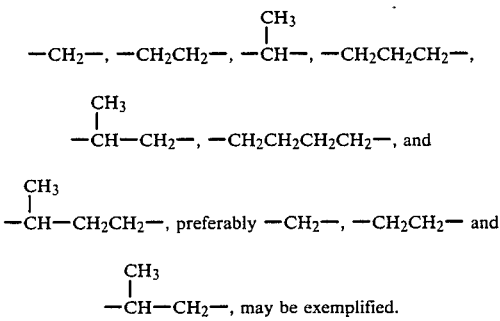

may be exemplified.

In the general formulae (II) to (V), R represents a hydrogen atom; a lower alkyl group, preferably ($C_1$-$C_4$) alkyl group, more preferably methyl group; or a lower alkoxy group, preferably ($C_1$-$C_4$) alkoxy group, more preferably methoxy group. $R^1$, $R^2$, $R^3$ and $R^4$ respectively represent a hydrogen atom or methyl group.

Preferred compounds of a substituted phenylurea compound represented by the general formula (II) are shown in Table 1. Further, compounds represented by the formula (II) wherein A represents a methylene group, an ethylene group or a propylene group; and R represents a methyl group or a methoxy group are preferable. Among these, compounds Nos. 3, 4, 8, 9, 20, 21, 26, 28 and 29 are more preferable.

Preferred compounds of a substituted phenylurea compound represented by the general formula (III) are shown in Tables 2 and 3. Further compounds represented by the formula (III) wherein A represents an ethylene group or a propylene group; R represents a methyl group or a methoxy group; and $R^1$ represents a methyl group are preferable. Among these, compounds Nos. 43, 44, 45, 49, 52 and 53 are more preferable.

Preferred compounds of a substituted pyridylurea derivative represented by the general formula (IV) are compounds Nos. 54 to 57. Further, compounds represented by the formula (IV) wherein A represents a methyl group; R represents a methyl group are preferable. Among these, compound No. 56 is more preferable.

Preferred compounds of a substituted phenylurea derivative represented by the general formula (V) are shown in Tables 4 to 7. Further, compounds represented by the the formula (V) wherein A represents a ethylene group or a propylene group; R represents a methyl group or a methoxy group; $R^1$ and $R^2$ respectively represent a hydrogen atom or a methyl group; and $R^3$ and $R^4$ respectively represent a hydrogen atom are preferable. Among these, compound Nos. 61, 73, 85, 93, 101 and 102 are more preferable.

(1) A compound represented by the general formula (II) according to the present invention is a novel compound and can be produced from various materials, for example, in accordance with the following reaction schemes.

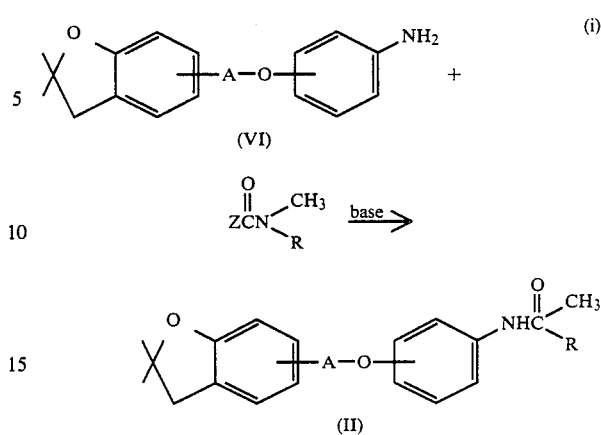

(wherein A and R are as defined above, and Z represents a halogen atom).

The above-described reaction is carried out without any solvent or in a solvent selected from the group consisting of: ketones such as acetone and ethylmethyl ketone; aromatic hydrocarbons such as benzene and toluene; ethers such as diethyl ether and tetrahydrofuran; and aprotic polar solvents such as acetonitrile, N,N-dimethylformamide, dimethyl sulfoxide and N-methylpyrrolidone at 0° to 150° C., preferably 0° to 50° C. for 0.5 to 6 hours in the presence of an organic base such as triethylamine, pyridine and N,N-diethylaniline, or an inorganic base such as sodium carbonate and sodium hydroxide.

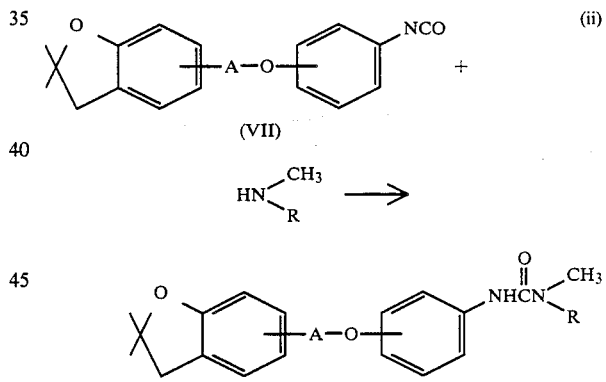

(wherein A and R are as defined above)

The above-described reaction is carried out without any solvent or in a solvent selected from the group consisting of: aromatic hydrocarbons such as benzene, toluene, xylene, and chlorobenzene; acetates such as ethyl acetate and isobutyl acetate; ethers such as diethyl ether, diisopropyl ether, tetrahydrofuran and dioxane; aprotic polar solvents such as N,N-dimethylformamide, dimethyl sulfoxide and N-methylpyrrolidone; ketones such as acetone and ethylmethyl ketone; alcohols such as methanol, ethanol and butanol; water; and a mixed solvent thereof at −50° to 100° C., preferably 0° to 50° C. for 0.5 to 12 hours.

An isocyanate (VII), which is the starting material for the above-described reaction can be produced from an aniline derivative (VI), which is the starting material for the reaction represented by the reaction scheme (i) in accordance with the following reaction scheme:

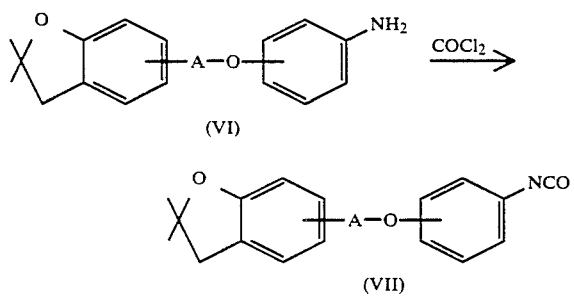

(VI)

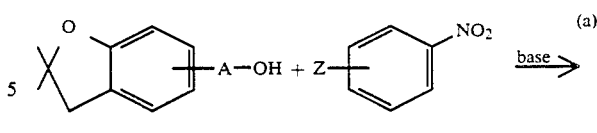

(a)

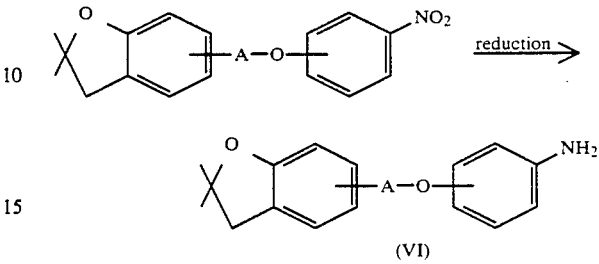

(VI)

(wherein A and Z are as defined above)

(wherein A is as defined above)

The above-described reaction is carried out in a solvent selected from the group consisting of: aromatic hydrocarbons such as benzene, toluene, xylene, and chlorobenzene; acetates such as ethyl acetate and isobutyl acetate; and ethers such as diethyl ether, diisopropyl ether, tetrahydrofuran and dioxane at $-20°$ to $180°$ C., preferably $0°$ to $120°$ C. for 2 to 15 hours in the presence or absence of an organic base such as triethylamine, pyridine, quinoline, N,N-diethylaniline.

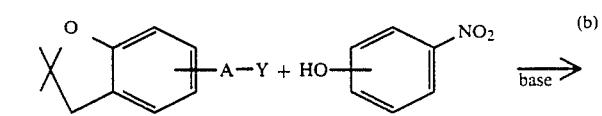

(iii)

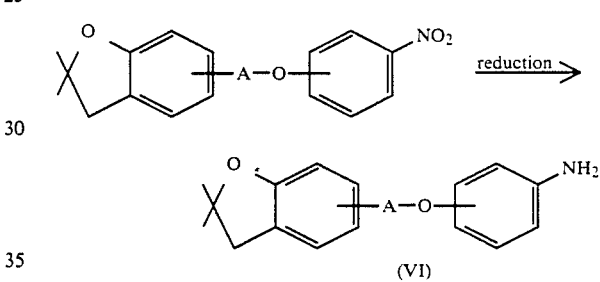

(VI)

(wherein A and Y are as defined above)

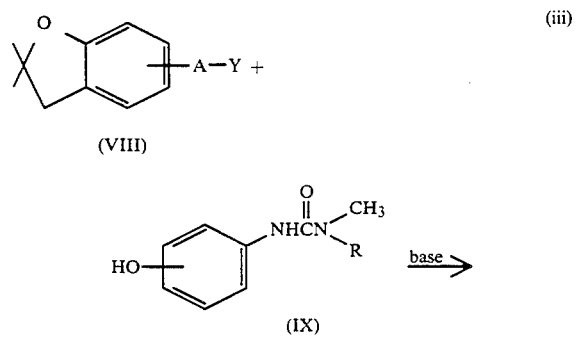

(II)

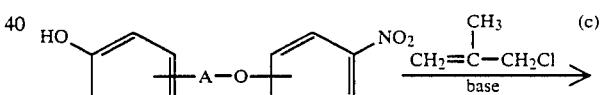

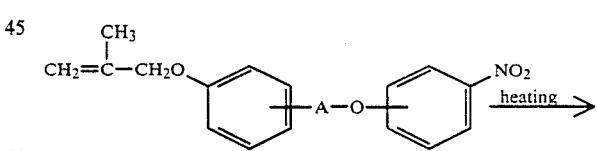

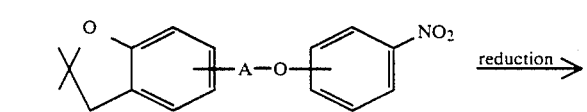

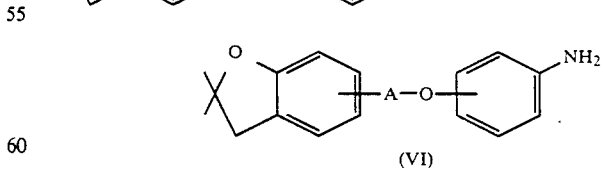

(VI)

(wherein A and Z are as defined above)

(wherein A and R are as defined above, and Y represents a halogen atom, an alkylsulfonyloxy group or an arylsulfonyloxy group).

The above-described reaction is carried out without any solvent or in a solvent selected from the group consisting of: ketones such as acetone and ethylmethyl ketone; aromatic hydrocarbons such as benzene and toluene; ethers such as diethyl ether and tetrahydrofuran; and aprotic polar solvents such as acetonitrile, N,N-dimethylformamide, dimethyl sulfoxide and N-methylpyrrolidone at $0°$ to $150°$ C., preferably $0°$ to $120°$ C. for 1 to 6 hours in the presence of an organic base such as triethylamine, pyridine and N,N-diethylaniline, an inorganic base such as sodium carbonate and sodium hydroxide, an alkali metal hydride such as sodium hydride or an alkali metal such as metal sodium.

An aniline derivative (VI), which is a starting material for the reactions shown in (i) and (ii) can be produced in accordance with the following reaction scheme (a), (b) or (c).

(2) A compound represented by the formula (III) according to the present invention is a novel compound, and can be produced from various materials by a process shown in (1).

For example,

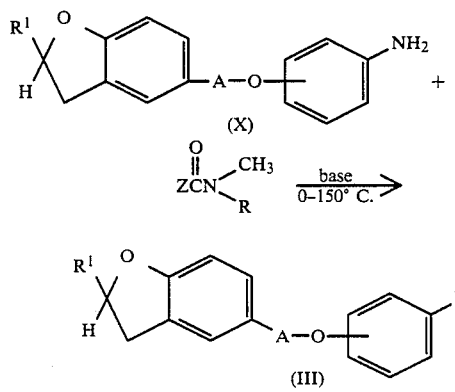

(wherein A, R and R¹ are as defined above, and Z represents a halogen atom)

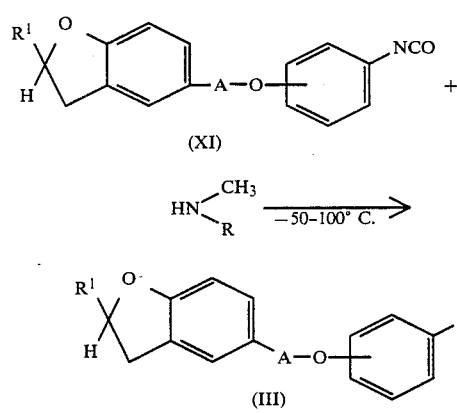

(wherein A, R and R¹ are as defined above)

An isocyanate derivative (XI), which is the starting material for the above-described reaction can be produced from an aniline derivative (X), which is the starting material for the reaction represented in accordance with a process shown in (1):

For example,

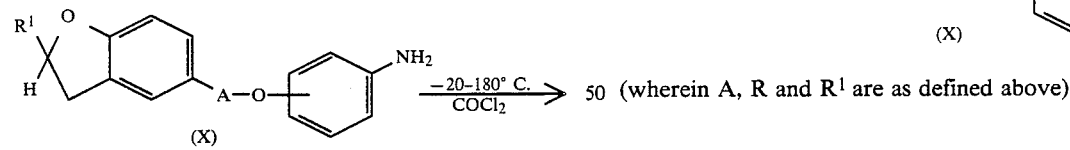

(wherein A and R¹ are as defined above)

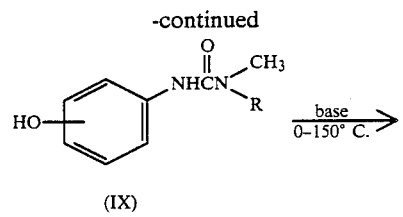

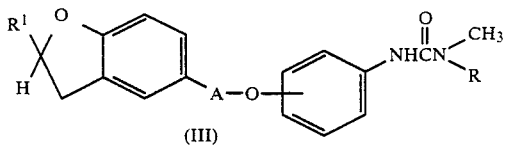

(wherein A, R and R¹ are as defined above, and Y represents a halogen atom, an alkylsulfonyloxy group or an arylsulfonyloxy group)

An aniline derivative (X), which is a starting material for the reactions represented by the reaction schemes (i) and (ii) can be produced by the following process (a) or (b):

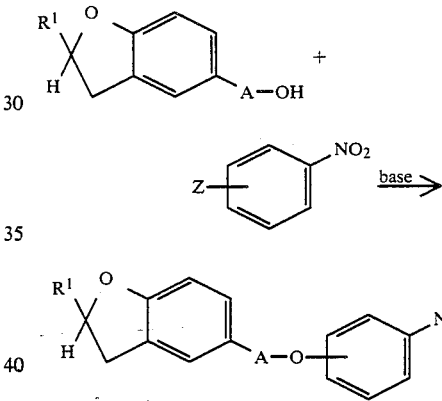

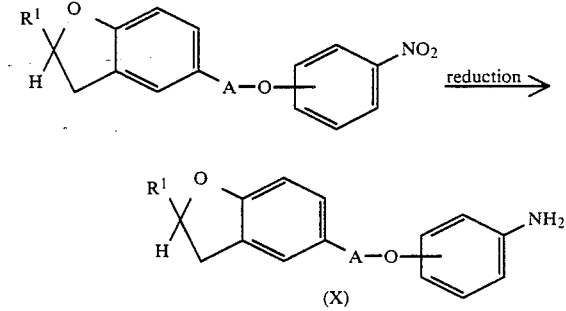

(wherein A, R and R¹ are as defined above)

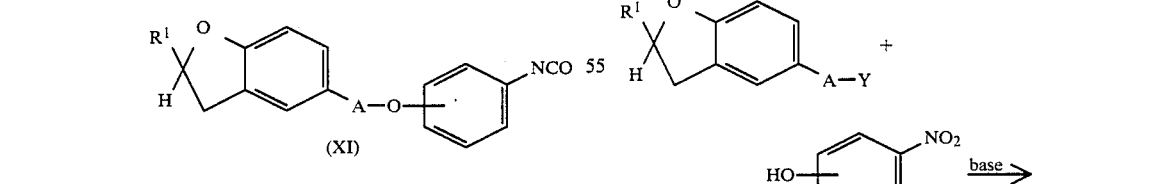

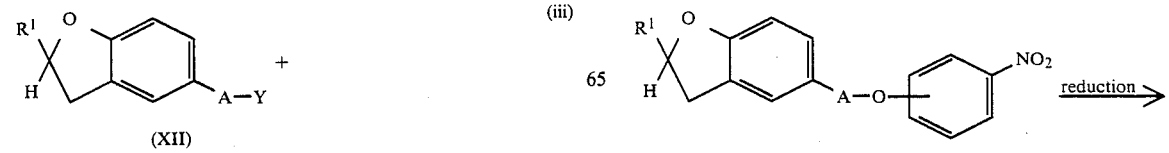

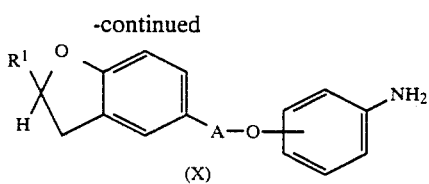

(wherein A, R and R¹ are as defined above)

(3) A compound represented by the general formula (IV) according to the present invention is a novel compound and can be produced from various materials, for example, in accordance with the following reaction schemes.

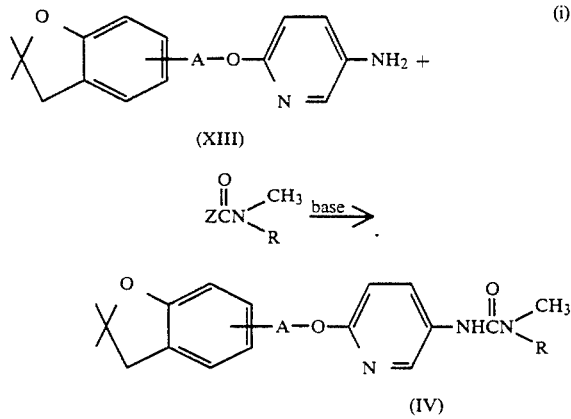

(wherein A and R are as defined above and Z represents a halogen atom)

The above-described reaction is carried out without any solvent or in a solvent selected from the group consisting of: ketones such as acetone and ethylmethyl ketone; aromatic hydrocarbons such as benzene and toluene; ethers such as diethyl ether and tetrahydrofuran; and aprotic polar solvents such as acetonitrile, N,N-dimethylformamide, dimethyl sulfoxide and N-methylpyrrolidone at 0° to 150° C., preferably 0° to 50° C. for 0.5 to 6 hours in the presence of an organic base such as triethylamine, pyridine and N,N-diethylaniline, or an inorganic base such as sodium carbonate and sodium hydroxide.

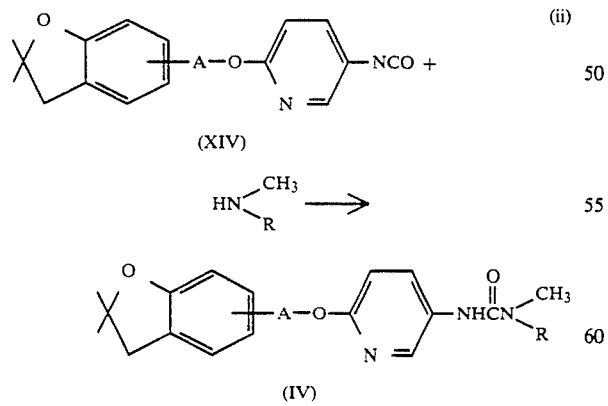

(wherein A and R are as defined above)

The above-described reaction is carried out without any solvent or in a solvent selected from the group consisting of: aromatic hydrocarbons such as benzene, toluene, xylene, and chlorobenzene; acetates such as ethyl acetate and isobutyl acetate; ethers such as diethyl ether, diisopropyl ether, tetrahydrofuran and dioxane; aprotic polar solvents such as N,N-dimethylformamide, dimethyl sulfoxide and N-methylpyrrolidone; ketones such as acetone and ethylmethyl ketone; alcohols such as methanol, ethanol and butanol; water; and a mixed solvent thereof at −50° to 100° C., preferably 0° to 50° C. for 0.5 to 12 hours.

An isocyanate derivative (XIV, which is a starting material for the above-described reaction can be produced from an aniline derivative (XIII), which is a starting material for the reaction represented by the reaction scheme (i) in accordance with the following reaction scheme:

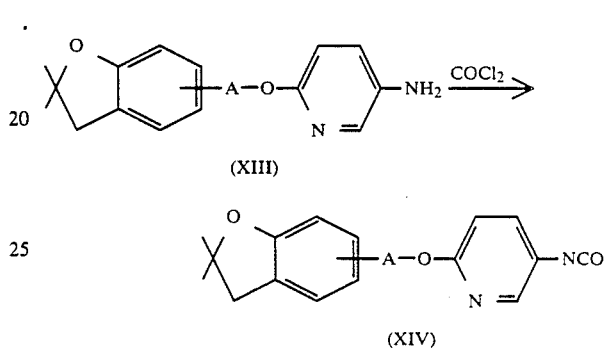

(wherein A is as defined above) The above-described reaction is carried out in a solvent selected from the group consisting of: aromatic hydrocarbons such as benzene, toluene, xylene, and chlorobenzene; acetates such as ethyl acetate and isobutyl acetate; and ethers such as diethyl ether, diisopropyl ether, tetrahydrofuran and dioxane at −20° to 180° C., preferably 0° to 120° C. for 2 to 15 hours in the presence or absence of an organic base such as triethylamine, pyridine, quinoline and N,N-diethylaniline.

An aniline derivative (XIII), which is a starting material for the reactions represented by the reaction schemes (i) and (ii) can be produced by the following process:

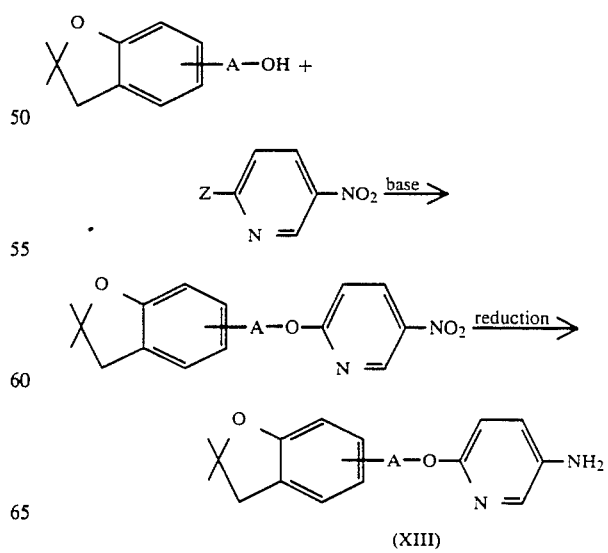

(wherein A and Z are as defined above)

(4) A compound represented by the formula (v) according to the present invention is a novel compound, and can be produced from various materials by a process shown in (1).

For example,

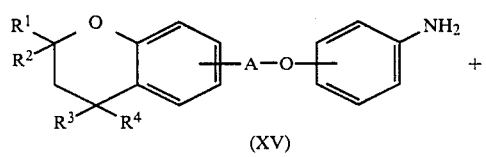
(XV)

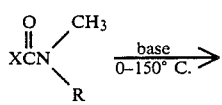

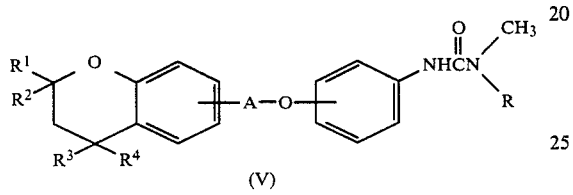
(V)

(wherein A, R, R¹, R², R³ and R⁴ are as defined above, and X represents a halogen atom)

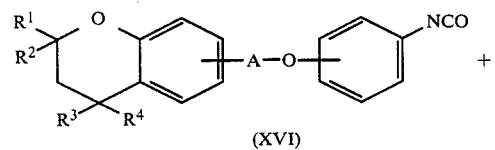
(XVI)

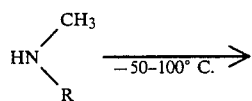

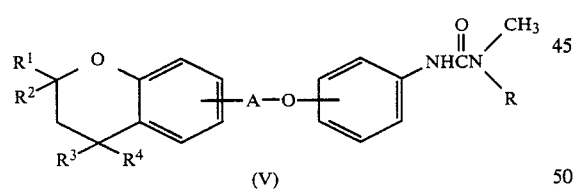
(V)

(wherein A, R, R¹, R², R³ and R⁴ are as defined above)

An isocyanate derivative (XVI), which is a starting material for the above-described reaction can be produced from an aniline derivative (XV), which is a starting material for the reaction represented by the reaction scheme (V) in accordance with the following reaction scheme:

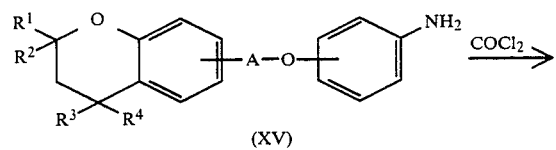
(XV)

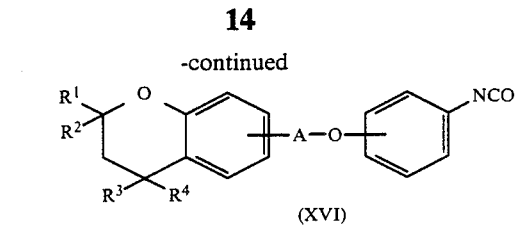
(XVI)

(wherein A, R¹, R², R³ and R⁴ are as defined above, and

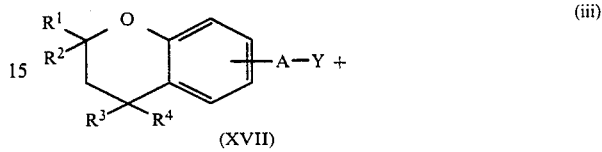
(XVII)

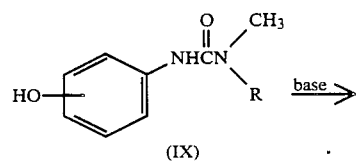
(IX)

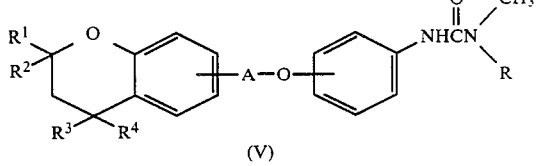
(V)

(wherein A, R, R¹, R², R³ and R⁴ are as defined above, and Y represents a halogen atom, an alkylsulfonyloxy group or an arylsulfonyloxy group)

An aniline derivative (XV), which is a starting material for the reactions represented by the reaction schemes (i) and (ii) can be produced by the following process (a) or (b):

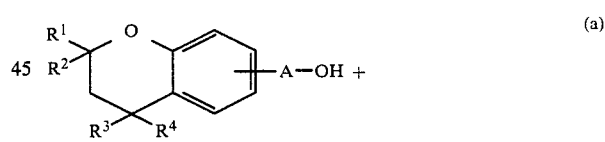

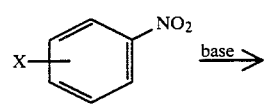

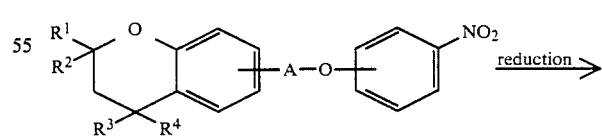

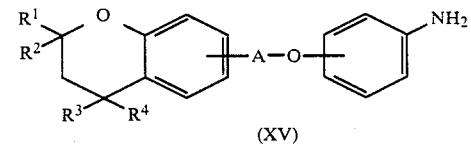
(XV)

(wherein A, R¹, R², R³, R⁴ and X are as defined above)

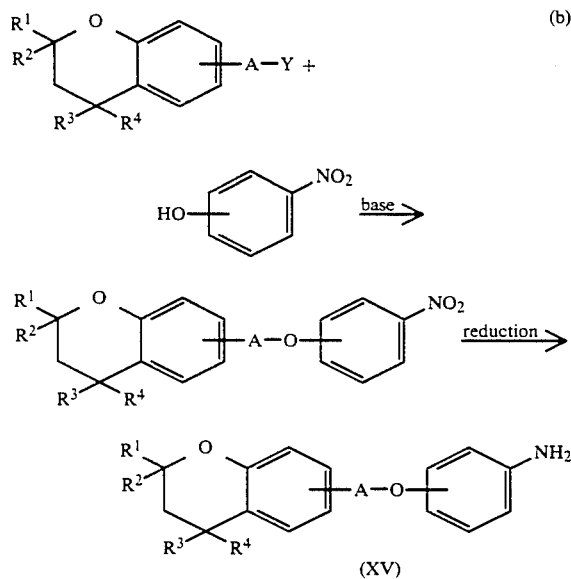

(wherein A, $R^1$, $R^2$, $R^3$, $R^4$ and Y are as defined above)

The thus-obtained compound according to the present invention can be used singly as a herbicide, but ordinarily, it is mixed with an inactive liquid or solid carrier and an appropriate surfactant or the like is added thereto so as to be used in the form of a composition such as emulsion, dust, granules and wettable powder.

As a liquid carrier, for example, toluene, xylene, methylnaphthalene, cyclohexane, butanol, glycol, dimethylsulfoxide, dimethylformamide, acetone, methylisobutyl ketone, animal and vegetable oils, fatty acids, fatty esters and water are usable. As a solid carrier, for example, clay, kaolin clay, talc, bentonite, diatomaceaous earth, silica, calcium carbonate, and vegetable flour such as soy bean flour and wheat flour are usable. Further, if necessary, the compound may be mixed before use with other active ingredients such as an agricultural germicide, insecticide and nematicide, or another herbicide, plant growth regulating agent, soil conditioner, and fertilizer. The compound also may be appropriately mixed with an adjuvant such as a spreader, emulsifier, wetting agent and fixing agent.

The appropriate amount of herbicidal composition of the present invention for use is different depending upon the kind of the compound used, weeds being killed, treating season, treating method, and the nurture of the soil, but the appropriate range is generally 0.5 to 80 g/are, preferably 1 to 50 g/are as an active ingredient.

A compound of the present invention shows a high herbicidal activity in upland field and paddy field without doing no practical harm to crops. More specifically, the herbicidal compositions containing the compounds of the present invention as active ingredients are capable of controlling weeds in upland fields, such as lambsquarters (*Chenopodium album*), goosefoot (*Chenopodium album* var. centrorubrum), persicaria blumei gross (*Polygonum blumei*), ladysthumb (*Polygonum persicaria*), livid amaranth (*Amaranthus lividus*), common purselane (*Portulaca oleracea*), common chickweed (*Stellaria media*), dead-nettle (*Lamium amplexicaule*), large crabgrass (*Digitaria sanguinalis*), goosegrass (*Eleusine indica*), green foxtail (*Setaria viridis*), water foxtail (*Alopecurus aequalis*) and flat-sedge (*Cyperus microiria*) and weeds in paddy fields, such as false pimpernel (*Lindernia procumbens*), toothcup (*Rotala indica*), abunome (*Dopatrium junceum*), american waterwort (*Elatine triandra*), narrowleaf waterplantain (*Alisma canaliculatum*), barnyardgrass (*Echinochloa crus-galli L. Beauv.* var. crus-galli), umbrella plant (*Cyperus difformis*) and duck-tongue weed (*Monochloria vaginalis*) by the preemergence treatment or by the treatment during the growing stage. Further, the compounds of the present invention can be used as selective herbicides for the cultivation of crop plants such as rice (*Oryza sative*), sunflower (*Helianthus annuus*), potato (*Salanum tuberosum*), wheat (*Triticum aestivum*), barley (*Hordeum vulgare*), sugar cane (*Saccharum officinarum*), and corn (*Zea mays*).

As described above, the compound of the present invention is excellent in that it is capable of controlling a number of weeds without substantially adversely affecting the crop plants.

Furthermore, the compound of the present invention has been proved to have a high herbicidal activity against weeds which have hitherto been considered to be difficult to hardly control, namely, weeds in upland field such as velvetleaf (*Abutilon theophrasti*), purpleflowered thornapple (*Datura tatula L.*), wild mustard (*Brassica kaber* var. pinnatifida), bedstraw (*Galium aparine*), western violet (*Viola sp.*), and pineappleweed (*Matricaria matricarioides*). Thus, the compound of the present invention has a very wide herbicidal spectrum and at the same time a high level of safety.

The present invention is explained in more detail in the following Examples; however, it should be recognized that the scope of the present invention is not restricted to these Examples.

EXAMPLE 1

1-[4-(2,3-dihydro-2,2-dimethyl-5-benzofuranylmethyloxy)phenyl]-3-methoxy-3-methylurea 6.9 g of 4-(2,3-dihydro-2,2-dimethyl-5-benzofuranylmethyloxy)aniline was dissolved into 30 ml of pyridine, and 3.8 g of N-methoxy-N-methylcarbamoyl chloride was slowly added dropwise thereto under cooling with ice. After 2-hours' continuous stirring, pyridine was distilled off under a reduced pressure, and the residual oily matter was dissolved into 100 ml of toluene. After the solution was subsequently washed with water, diluted hydrochloric acid and saturated sodium chloride aqueous solution, toluene was distilled off. The residue was subjected to silica gel column chromatography using ethyl acetate/n-hexane (¼) as a developing solvent (developer) to obtain 7.6 g of Compound No. 2 shown in Table 1.

EXAMPLE 2

1-[4-(2,3-dihydro-2,2-dimethyl-6-benzofuranylmethyloxy)phenyl]-3-methoxy-3-methylurea 6.9 g of 4-(2,3-dihydro-2,2-dimethyl-6-benzofuranylmethyloxy)aniline was dissolved into 70 ml of N,N-dimethylformamide, and 2.8 g of triethylamine was added thereto. 3.8 g of N-methoxy-N-methylcarbamoyl chloride was slowly added dropwise thereto. After the mixture was stirred at room temperature, the reaction mixture was poured into water and extracted with ethyl acetate. After the organic layer was washed with water, it was dried over anhydrous magnesium sulfate. Ethyl acetate was distilled off and the residue was subjected to silica gel column chromatography using ethyl acetate/n-hexane (½) as a developer to obtain 6.0 g of Compound No. 4 shown in Table 1.

EXAMPLE 3

1-[4-(2,3-dihydro-2,2-dimethyl-4-benzofuranylmethyloxy)phenyl]-3-methoxy-3-methylurea

1.8 g of 4-(2,3-dihydro-2,2-dimethyl-4-benzofuranylmethyloxy)phenyl isocyanate was dissolved into 20 ml of toluene, and 2.0 g of N,O-dimethylhydroxylamine dissolved in 5 ml of toluene was slowly added dropwise thereto at room temperature. After the mixture was stirred at room temperature for 2 hours, toluene was distilled off and the residue was subjected to silica gel column chromatography using ethyl acetate/n-hexane (½) as a developer to obtain 1.8 g of Compound No. 6 shown in Table 1.

EXAMPLE 4

1-[4-(2,3-dihydro-2,2-dimethyl-7-benzofuranylmethyloxy)phenyl]-3,3-dimethylurea

3.0 g of 2,3-dihydro-2,2-dimethyl-7-benzofuranylmethyl chloride and 3.0 g of 1-(4-hydroxyphenyl)-3,3-dimethylurea were dissolved into 20 ml of dried N,N-dimethylformamide, and 2.5 g of anhydrous potassium carbonate was added thereto. After the mixture was stirred at 80° C. for 4 hours, the reaction mixture was poured into water and extracted with ethyl acetate. After the organic layer was washed with water, it was dried over anhydrous magnesium sulfate and ethyl acetate was distilled off. The residue was subjected to silica gel column chromatography using ethyl acetate/n-hexane (1/1) as a developer to obtain 4.0 g of Compound No. 7 shown in Table 1.

EXAMPLE 5

1-[4-[2-(2,3-dihydro-2,2-dimethyl-7-benzofuranyl)ethyloxy]phenyl]-3-methoxy-3-methylurea

2.6 g of 1-(4-hydroxyphenyl)-3-methoxy-3-methylurea was dissolved into 20 ml of dried N,N-dimethylformamide, and 0.6 g of 60% sodium hydride was added thereto. After the mixture was stirred for 30 minutes, 1.7 g of 2-(2,3-dihydro-2,2-dimethyl-7-benzofuranyl)ethyl chloride was added dropwise thereto under cooling with ice. After the mixture was stirred at room temperature for 5 hours, it was poured into water and extracted with ethyl acetate. After the organic layer was washed with water, it was dried over anhydrous magnesium sulfate and ethyl acetate was distilled off. The residue was subjected to silica gel column chromatography using ethyl acetate/n-hexane (1/1) as a developer to obtain 2.0 g of Compound No. 10 shown in Table 1.

The compounds shown in Table 1 were produced in the same manner as in Examples 1 to 5. Table 1 also shows the melting point or the refractive index of each compound.

TABLE 1

| No. | Structural formula | Melting Point or Refractive Index |
|---|---|---|
| 1 | (structure) | 164–166° C. |
| 2 | (structure) | 132–133° C. |
| 3 | (structure) | 90–93° C. |
| 4 | (structure) | $n_D^{24}$ 1.5559 |

TABLE 1-continued

| No. | Structural formula | Melting Point or Refractive Index |
|---|---|---|
| 5 | | 166–168° C. |
| 6 | | 86–88° C. |
| 7 | | 132–133° C. |
| 8 | | 83–85° C. |
| 9 | | 83–85° C. |
| 10 | | $n_D^{24}$ 1.5550 |

TABLE 1-continued

| No. | Structural formula | Melting Point or Refractive Index |
|---|---|---|
| 11 | | 89–90° C. |
| 12 | | $n_D^{24}$ 1.5600 |
| 13 | | 139–141° C. |
| 14 | | 129–130° C. |
| 15 | | 145–146° C. |
| 16 | | 92–94° C. |
| 17 | | 101–102° C. |
| 18 | | 126.5–127.5° C. |

TABLE 1-continued

| No. | Structural formula | Melting Point or Refractive Index |
|---|---|---|
| 19 | (structure) | 142–143° C. |
| 20 | (structure) | 66–67° C. |
| 21 | (structure) | 120–121° C. |
| 22 | (structure) | 124–125° C. |
| 23 | (structure) | 106–107° C. |
| 24 | (structure) | $n_D^{24}$ 1.5620 |
| 25 | (structure) | 111–112° C. |
| 26 | (structure) | $n_D^{24}$ 1.5579 |
| 27 | (structure) | 106–107° C. |

TABLE 1-continued

| No. | Structural formula | Melting Point or Refractive Index |
|-----|--------------------|-----------------------------------|
| 28 | (structure) | $n_D^{24}$ 1.5535 |
| 29 | (structure) | 89–90° C. |
| 30 | (structure) | $n_D^{23}$ 1.5647 |
| 31 | (structure) | 120–120.5° C. |
| 32 | (structure) | $n_D^{25}$ 1.5641 |
| 33 | (structure) | 113–115° C. |
| 34 | (structure) | 110.5–111.5° C. |
| 35 | (structure) | 75–80° C. |

TABLE 1-continued

| No. | Structural formula | Melting Point or Refractive Index |
|---|---|---|
| 36 | (structure) | 119–120° C. |
| 37 | (structure) | 129–131° C. |
| 38 | (structure) | $n_D^{23}$ 1.5468 |
| 39 | (structure) | 122–124° C. |

EXAMPLE 6

1-[4-(2,3-dihydro-2-methyl-5-benzofuranylmethyloxy)-phenyl]-3-methoxy-3-methylurea 6.5 g of 4-(2,3-dihydro-2-methyl-5-benzofuranylmethyloxy)aniline was dissolved into 30 ml of pyridine, and 3.8 g of N-methoxy-N-methylcarbamoyl chloride was slowly added dropwise thereto under cooling with ice. After 2-hours' continuous stirring, pyridine was distilled off under a reduced pressure, and the residual oily matter was dissolved into 100 ml of toluene. After the reaction mixture was subsequently washed with water, diluted hydrochloric acid and saturated sodium chloride aqueous solution, toluene was distilled off. The residue was subjected to silica gel column chromatography using ethyl acetate/n-hexane (1/1) as a developer to obtain 7.3 g of Compound No. 40 shown in Table 2.

EXAMPLE 7

1-[4-(2,3-dihydro-2-methyl-5-benzofuranylmethyloxy)-phenyl]-3,3-dimethylurea 6.5 g of 4-(2,3-dihydro-2-methyl-5-benzofuranylmethyloxy)aniline was dissolved into 70 ml of N,N-dimethylformamide, and 2.8 g of triethylamine was added thereto. 3.8 g of N,N-dimethylcarbamoyl chloride was slowly added dropwise thereto. After the mixture was stirred at room temperature, the reaction mixture was poured into water and extracted with ethyl acetate. After the organic layer was washed with water, it was dried over anhydrous magnesium sulfate and ethyl acetate was distilled off. The residue was subjected to silica gel column chromatography using ethyl acetate/n-hexane (2/1) as a developer to obtain 5.8 g of Compound No. 41 shown in Table 2.

EXAMPLE 8

1-{4-[2-(2,3-dihydro-2-methyl-5-benzofuranyl)ethyloxy]phenyl}-3-methoxy-3-methylurea 1.8 g of 4-[2-(2,3-dihydro-2-methyl-5-benzofuranyl)ethyloxy]phenyl isocyanate was dissolved into 20 ml of toluene, and 2.0 g of N,O-dimethylhydroxylamine dissolved in 5 ml of toluene was slowly added dropwise thereto at room temperature. After the mixture was stirred at room temperature for 2 hours, toluene was distilled off and the residue was subjected to silica gel column chromatography using ethyl acetate/n-hexane (2/3) as a developer to obtain 1.8 g of Compound No. 42 shown in Table 2.

EXAMPLE 9

1-[3-(2,3-dihydro-2-methyl-5-benzofuranylmethyloxy)-phenyl]-3-methoxy-3-methylurea 2.8 g of 2,3-dihydro-2-methyl-5-benzofuranylmethyl chloride and 3.0 g of 1-(3-hydroxyphenyl)-3-methoxy-3-methylurea were dissolved into 20 ml of dried N,N-dimethylformamide, and 2.5 g of anhydrous potassium carbonate was added thereto. After the mixture was stirred at 80° C. for 4 hours, the reaction mixture was poured into water and extracted with ethyl acetate. After the organic layer was washed with water, it was dried over anhydrous magnesium sulfate and ethyl acetate was dried off. The residue was subjected to silica gel column chromatography using ethyl acetate/n-hexane (½) as a developer to obtain 3.7 g of Compound No. 46 shown in Table 2.

EXAMPLE 10

1-{-[2-(2,3-dihydro-2-methyl-5-benzofuranyl)ethyloxy]-phenyl}-3-methoxy-3-methylurea 2.0 g of 1-(3-hydroxyphenyl)-3-methoxy-3-methylurea was dissolved into 20 ml of dried N,N-dimethylformamide, and 0.4 g of 60% sodium hydride was added thereto. After the mixture was stirred for 30 minutes, 3.3 g of 2-(2,3-dihydro-2-methyl-5-benzofuranyl)ethyl-p-toluene sulfonate was added dropwise thereto under cooling with ice. After the mixture was stirred at room temperature for 5 hours, it was poured into water and extracted with ethyl acetate. After the organic layer was washed with water, it was dried over anhydrous magnesium sulfate and ethyl acetate was distilled off. The residue was subjected to silica gel column chromatography using ethyl acetate/n-hexane (½) as a developer to obtain 3.3 g of Compound No. 49 shown in Table 3.

The compounds shown in Tables 2 and 3 were produced in the same manner as in Examples 6 to 10. Tables 2 and 3 also show the melting point or the refractive index of each compound.

TABLE 2

| No. | R | R¹ | A | Melting Point or Refractive Index |
|---|---|---|---|---|
| 40 | —OCH$_3$ | —CH$_3$ | —CH$_2$— | 100–102° C. |
| 41 | —CH$_3$ | —CH$_3$ | —CH$_2$— | 154–155° C. |
| 42 | —OCH$_3$ | —CH$_3$ | —CH$_2$CH$_2$— | 114–116° C. |
| 43 | —CH$_3$ | —CH$_3$ | —CH$_2$CH$_2$— | 95–96° C. |
| 44 | —OCH$_3$ | —CH$_3$ | —CHCH$_2$—<br>   $\vert$<br>   CH$_3$ | $n_D^{24}$ 1.5652 |
| 45 | —CH$_3$ | —CH$_3$ | —CHCH$_2$—<br>   $\vert$<br>   CH$_3$ | 131–134° C. |

TABLE 3

| No. | R | R¹ | A | Melting Point or Refractive Index |
|---|---|---|---|---|
| 46 | —OCH$_3$ | —CH$_3$ | —CH$_2$— | 72–73° C. |
| 47 | —CH$_3$ | —CH$_3$ | —CH$_2$— | 133.5–134.5° C. |
| 48 | —H | —CH$_3$ | —CH$_2$CH$_2$— | 90–91° C. |
| 49 | —OCH$_3$ | —CH$_3$ | —CH$_2$CH$_2$— | $n_D^{24}$ 1.5645 |
| 50 | —OC$_2$H$_5$ | —CH$_3$ | —CH$_2$CH$_2$— | $n_D^{24}$ 1.5648 |
| 51 | —CH$_3$ | —CH$_3$ | —CH$_2$CH$_2$— | 104–106° C. |
| 52 | —OCH$_3$ | —CH$_3$ | —CHCH$_2$—<br>   $\vert$<br>   CH$_3$ | $n_D^{24}$ 1.5655 |
| 53 | —CH$_3$ | —CH$_3$ | —CHCH$_2$—<br>   $\vert$<br>   CH$_3$ | $n_D^{24}$ 1.5790 |

EXAMPLE 11

1-[2-(2,3-dihydro-2,2-dimethyl-7-benzofuranylmethyloxy)-5-pyridyl]-3-methoxy-3-methylurea (Compound No. 54):

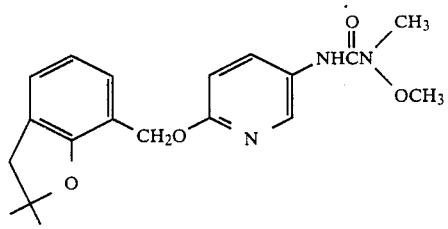

2.0 g of 2-(2,3-dihydro-2,2-dimethyl-7-benzofuranylmethyloxy)-5-aminopyridine was dissolved into 5 ml of pyridine, and 1.1 g of N-methoxy-N-methylcarbamoyl chloride was slowly added dropwise thereto under cooling with ice. After 2-hours' continuous stirring, pyridine was distilled off under a reduced pressure, and the residual oily matter was dissolved into 30 ml of toluene. After the mixture was subsequently washed with water, diluted hydrochloric acid and saturated sodium chloride aqueous solution, toluene was distilled off. The residue was subjected to silica gel column chromatography using ethyl acetate/n-hexane (1/1) as a developer to obtain 2.2 g of 1-[2-(2,3-dihydro-2,2-dimethyl-7-benzofuranylmethyloxy)-5-pyridyl]-3-methoxy-3-methylurea.

Refractive index $n_D^{25}$ = 1.5634.

EXAMPLE 12

1-{2-[2-(2,3-dihydro-2,2-dimethyl-5-benzofuranyl)ethyloxy]-5-pyridyl}-3-methoxy-3-methylurea (Compound No. 55):

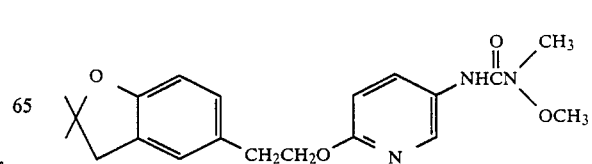

2.2 g of 2-[2-(2,3-dihydro-2,2-dimethyl-5-benzofuranyl)ethoxy]-5-aminopyridine was dissolved into 10 ml of N,N-dimethylformamide, and 0.9 g of triethylamine was added thereto. 1.2 g of N-methoxy-N-methylcarbamoyl chloride was slowly added dropwise thereto. After the mixture was stirred at room temperature, the reaction mixture was poured into water and extracted with ethyl acetate. After the organic layer was washed with water, it was dried over anhydrous magnesium sulfate and ethyl acetate was dried off. The residue was subjected to silica gel column chromatography using ethyl acetate/n-hexane (2/3) as a developer to obtain 2.1 g of 1-{2-[2-(2,3-dihydro-2,2-dimethyl-5-benzofuranyl)ethoxy]-5-pyridyl}-3-methoxy-3-methylurea.

Melting point: 79° to 80° C.

EXAMPLE 13

1-[2-(2,3-dihydro-2,2-dimethyl-7-benzofuranylmethyloxy)-5-pyridyl]-3,3-dimethylurea (Compound No. 56):

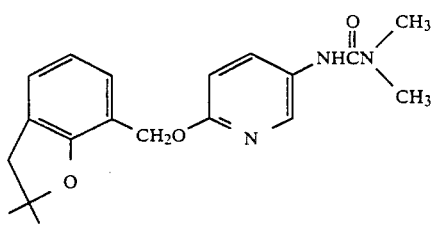

Compound No. 56 was synthesized in the same manner as in Example 11.

Melting point: 127.5° to 128.5° C.

EXAMPLE 14

1-{2-[2-(2,3-dihydro-2,2-dimethyl-5-benzofuranyl)ethyloxy]-5-pyridyl}-3,3-dimethylurea (Compound No. 57):

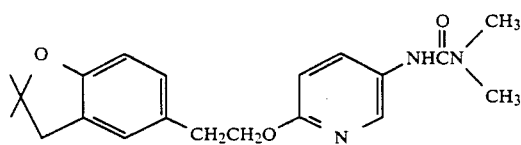

Compound No. 57 was synthesized in the same manner as in Example 11.

Melting point: 153° to 154° C.

EXAMPLE 15

1-{4-[(3,4-dihydro-2H-1-benzopyran-6-yl)methyloxy]phenyl}-3-methoxy-3-methylurea 2.6 g of 4-[3,4-dihydro-2H-1-benzopyran-6-yl)methyloxy]aniline was dissolved into 15 ml of pyridine, and 1.5 g of N-methoxy-N-methylcarbamoyl chloride was slowly added dropwise thereto under cooling with ice. After 2-hours' stirring at room temperature, the reaction mixture was poured into iced water and extracted with ethyl acetate. After the organic layer was subsequently washed with diluted hydrochloric acid and saturated sodium chloride aqueous solution, it was dried over anhydrous sodium sulfate.

Ethyl acetate was distilled off under a reduced pressure, and the residue was recrystallized from cyclohexane to obtain 2.9 g of Compound No. 58 shown in Table 4.

EXAMPLE 16

1-{4-[(3,4-dihydro-2-methyl-2H-1-benzopyran-6-yl)ethyloxy]phenyl}-3,3-dimethylurea 3.1 g of 4-[(3,4-dihydro-2-methyl-2H-1-benzopyran-6-yl)ethyloxy]phenyl isocyanate was dissolved into 30 ml of toluene, and 0.9 g of dimethylamine dissolved in 5 ml of toluene was slowly added dropwise thereto at room temperature. After the mixture was stirred at room temperature for 2 hours, toluene was distilled off under a reduced pressure and the residue was recrystallized from ethyl acetate to obtain 2.7 g of Compound No. 67 shown in Table 4.

EXAMPLE 17

1-{3-[(3,4-dihydro-2,2-dimethyl-2H-1-benzopyran-6-yl)methyloxy]phenyl}-3-methoxy-3-methylurea 2.0 g of 1-(3-hydroxyphenyl)-3-methoxy-3-methylurea was dissolved into 20 ml of dried N,N-dimethylformamide, and 0.4 g of 60% sodium hydride was added thereto. After the mixture was stirred for 15 minutes, 2.1 g of 3-[(3,4-dihydro-2,2-dimethyl-2H-1-benzopyran-6-yl)methyl]chloride was added dropwise thereto under cooling with ice. After the mixture was stirred at room temperature for 3 hours, it was poured into iced water and extracted with ethyl acetate. After the organic layer was washed with water, it was dried over anhydrous sodium sulfate and ethyl acetate was distilled off under a reduced pressure. The residue was purified by silica gel column chromatography using ethyl acetate/n-hexane (3/1) as a developer to obtain 2.6 g of Compound No. 91 shown in Table 5.

EXAMPLE 18

1-{3-[(3,4-dihydro-2,2-dimethyl-2H-1-benzopyran-6-yl)ethyloxy]phenyl}-3,3-dimethylurea 1.8 g of 1-(3-hydroxyphenyl)-3,3-dimethylurea was dissolved into 20 ml of dried N,N-dimethylformamide, and 0.4 g of 60% sodium hydride was added thereto. After the mixture was stirred for 15 minutes, 3.6 g of 3-[(3,4-dihydro-2,2-dimethyl-2H-1-benzopyran-6-yl)ethyl]-p-toluene sulfonate was added dropwise thereto under cooling with ice. After the mixture was stirred at room temperature for 5 hours, it was poured into iced water and extracted with ethyl acetate. After the organic layer was washed with water, it was dried over anhydrous sodium sulfate and ethyl acetate was distilled off. The residue was purified by silica gel column chromatography using n-hexane/ethyl acetate (1/1) as a developer to obtain 2.4 g of Compound No. 94 shown in Table 5.

The compounds shown in Tables 4 to 9 were produced in the same manner as in Examples 15 to 18. Tables 4 to 9 also show a physical property of each compound.

TABLE 4

[Structure: chroman with R¹,R² on C2, R³,R⁴ on C4, linked via A-O to phenyl bearing NHC(O)N(CH₃)R]

| No. | R¹ | R² | R³ | R⁴ | R | A | Physical property |
|---|---|---|---|---|---|---|---|
| 58 | H | H | H | H | —OCH₃ | —CH₂— | mp 109–110° C. |
| 59 | H | H | H | H | CH₃ | —CH₂— | mp 150–151° C. |
| 60 | H | H | H | H | —OCH₃ | —CH₂CH₂— | mp 115–116° C. |
| 61 | H | H | H | H | CH₃ | —CH₂CH₂— | mp 128–129° C. |
| 62 | H | H | H | H | —OCH₃ | —CH(CH₃)—CH₂— | mp 99–101° C. |
| 63 | H | H | H | H | CH₃ | —CH(CH₃)—CH₂— | mp 134–135° C. |
| 64 | CH₃ | H | H | H | —OCH₃ | —CH₂— | mp 128–129° C. |
| 65 | CH₃ | H | H | H | CH₃ | —CH₂— | mp 142–143° C. |
| 66 | CH₃ | H | H | H | —OCH₃ | —CH₂CH₂— | mp 118–119° C. |
| 67 | CH₃ | H | H | H | CH₃ | —CH₂CH₂— | mp 136–137° C. |
| 68 | CH₃ | H | H | H | CH₃ | —CH(CH₃)—CH₂— | mp 136–138° C. |
| 69 | CH₃ | CH₃ | H | H | —OCH₃ | —CH₂— | mp 110–111° C. |
| 70 | CH₃ | CH₃ | H | H | CH₃ | —CH₂— | mp 167–168° C. |
| 71 | CH₃ | CH₃ | H | H | —OCH₃ | —CH₂CH₂— | mp 107.5–108.5° C. |
| 72 | CH₃ | CH₃ | H | H | CH₃ | —CH₂CH₂— | mp 123–124° C. |
| 73 | CH₃ | CH₃ | H | H | —OCH₃ | —CH(CH₃)—CH₂— | mp 58–60° C. |
| 74 | CH₃ | CH₃ | H | H | CH₃ | —CH(CH₃)—CH₂— | mp 152–153° C. |
| 75 | CH₃ | CH₃ | H | H | —OCH₃ | —CH₂CH₂CH₂— | mp 105–106° C. |
| 76 | CH₃ | CH₃ | H | H | CH₃ | —CH₂CH₂CH₂— | mp 163–164° C. |
| 77 | H | H | CH₃ | CH₃ | —OCH₃ | —CH₂— | mp 131–132° C. |
| 78 | H | H | CH₃ | CH₃ | CH₃ | —CH₂— | mp 111–112° C. |
| 79 | H | H | CH₃ | CH₃ | —OCH₃ | —CH₂CH₂— | Amorphous |
| 80 | H | H | CH₃ | CH₃ | CH₃ | —CH₂CH₂— | mp 159–160° C. |

TABLE 5

[Structure: chroman with R¹,R² on C2, R³,R⁴ on C4, linked via A-O to meta-substituted phenyl bearing NHC(O)N(CH₃)R]

| No. | R¹ | R² | R³ | R⁴ | R | A | Physical Property |
|---|---|---|---|---|---|---|---|
| 81 | H | H | H | H | —OCH₃ | —CH₂ | mp 87–88° C. |
| 82 | H | H | H | H | CH₃ | —CH₂ | mp 125–126° C. |
| 83 | H | H | H | H | —OCH₃ | —CH₂CH₂— | mp 89–90° C. |
| 84 | H | H | H | H | CH₃ | —CH₂CH₂— | mp 99–100° C. |
| 85 | H | H | H | H | —OCH₃ | —CH(CH₃)—CH₂— | mp 96–98° C. |
| 86 | H | H | H | H | CH₃ | —CH(CH₃)—CH₂— | mp 126–127° C. |
| 87 | CH₃ | H | H | H | —OCH₃ | —CH₂— | mp 104–105° C. |
| 88 | CH₃ | H | H | H | CH₃ | —CH₂— | mp 163–164° C. |

TABLE 5-continued

Structure: R¹R² substituted chromanyl-A-O-phenyl-NHC(=O)N(CH₃)R

| No. | R¹ | R² | R³ | R⁴ | R | A | Physical Property |
|---|---|---|---|---|---|---|---|
| 89 | CH₃ | H | H | H | —OCH₃ | —CH₂CH₂— | mp 80–81° C. |
| 90 | CH₃ | H | H | H | CH₃ | —CH₂CH₂— | mp 134–135° C. |
| 91 | CH₃ | CH₃ | H | H | —OCH₃ | —CH₂— | mp 137–138° C. |
| 92 | CH₃ | CH₃ | H | H | CH₃ | —CH₂— | mp 147–147.5° C. |
| 93 | CH₃ | CH₃ | H | H | —OCH₃ | —CH₂CH₂— | mp 64.5–65° C. |
| 94 | CH₃ | CH₃ | H | H | CH₃ | —CH₂CH₂— | mp 133–134° C. |
| 95 | CH₃ | CH₃ | H | H | —OCH₃ | —CH(CH₃)—CH₂— | mp 96–97° C. |
| 96 | CH₃ | CH₃ | H | H | CH₃ | —CH(CH₃)—CH₂— | mp 128–129° C. |
| 97 | CH₃ | CH₃ | H | H | —OCH₃ | —CH₂CH₂CH₂— | mp 102–103° C. |
| 98 | CH₃ | CH₃ | H | H | CH₃ | —CH₂CH₂CH₂— | mp 130–131° C. |
| 99 | H | H | CH₃ | CH₃ | —OCH₃ | —CH₂— | $n_D^{25}$ 1.5740 |
| 100 | H | H | CH₃ | CH₃ | CH₃ | —CH₂— | mp 116–117° C. |
| 101 | H | H | CH₃ | CH₃ | —OCH₃ | —CH₂CH₂— | $n_D^{25}$ 1.5700 |
| 102 | H | H | CH₃ | CH₃ | CH₃ | —CH₂CH₂— | Amorphous |

TABLE 6

| No. | R¹ | R² | R³ | R⁴ | R | A | Physical Property |
|---|---|---|---|---|---|---|---|
| 103 | CH₃ | CH₃ | H | H | —OCH₃ | —CH₂— | $n_D^{25}$ 1.5692 |
| 104 | CH₃ | CH₃ | H | H | —OCH₃ | —CH₂CH₂— | mp 93–94° C. |
| 105 | CH₃ | CH₃ | H | H | CH₃ | —CH₂CH— | mp 142–143° C. |

TABLE 7

| No. | R¹ | R² | R³ | R⁴ | R | A | Physical Property |
|---|---|---|---|---|---|---|---|
| 106 | CH₃ | CH₃ | H | H | —OCH₃ | —CH₂— | $n_D^{25}$ 1.5662 |
| 107 | CH₃ | CH₃ | H | H | CH₃ | —CH₂— | mp 116–117° C. |
| 108 | CH₃ | CH₃ | H | H | —OCH₃ | —CH₂CH₂— | mp 56–58° C. |
| 109 | CH₃ | CH₃ | H | H | CH₃ | —CH₂CH₂— | mp 146–147° C. |

TABLE 8

| No. | R¹ | R² | R³ | R⁴ | R | A | Physical Property |
|---|---|---|---|---|---|---|---|
| 110 | CH₃ | CH₃ | H | H | —OCH₃ | —CH₂CH₂— | $n_D^{25}$ 1.5608 |
| 111 | CH₃ | CH₃ | H | H | CH₃ | —CH₂CH₂— | $n_D^{25}$ 1.5585 |

TABLE 9

| No. | R¹ | R² | R³ | R⁴ | R | A | Physical Property |
|---|---|---|---|---|---|---|---|
| 112 | H | H | H | H | —OCH₃ | —CH₂— | mp 105–106° C. |
| 113 | CH₃ | CH₃ | H | H | —OCH₃ | —CH₂CH₂— | $n_D^{25}$ 1.5597 |
| 114 | CH₃ | CH₃ | H | H | CH₃ | —CH₂CH₂— | mp 102–104° C. |

Formulation Examples for preparing a herbicide from a compound according to the present invention are set forth below. "Part" and "%" hereinunder represent "part by weight" and "% by weight", respectively.

FORMULATION EXAMPLE 1 (WETTABLE POWDER)

40 parts of a compound of the present invention, 20 parts of Caprex #80 (trade name, produced by Shionogi & Co., Ltd.), 35 parts of N,N Kaolinclay (trade mark, produced by Tsuchiya Kaolin Co., Ltd.) and 5 parts of a higher alcohol sulfate surfactant Solbol 8070 (trade mark, produced by Toho Chemical Co., Ltd.) were uniformly mixed and pulverized to obtain a wettable powder containing 40% of an active ingredient.

FORMULATION EXAMPLE 2 (GRANULES)

1 part of a compound of the present invention, 43 parts of clay (produced by Nihon Talc Co., Ltd.), 55 parts of bentonite (produced by Hojun Yoko Co., Ltd.) and 1 part of a succinate surfactant Airol CT-1 (produced by Toho Chemical Co., Ltd.) were mixed and pulverized. The resultant mixture was kneaded with 20 parts of water and extruded from the nozzles 0.6 mm in diameter of an extrusion pelletizer. The extruded pieces were dried at 60° C. for 2 hours and were then cut into a length of 1 to 2 mm, thereby obtaining granules containing 1% of an active ingredient.

FORMULATION EXAMPLE 3 (EMULSION)

An emulsion containing 30% of an active ingredient was prepared by dissolving 30 parts of a compound of the present invention into a mixed solvent of 30 parts of xylene and 25 parts of dimethylformamide, and adding 15 parts of polyoxyethylene surfactant Solbol 3005X (trade mark, produced by Toho Chemical Co., Ltd.).

FORMULATION EXAMPLE 4 (FLOWABLE AGENT)

30 parts of a compound of the present invention was adequately mixed with and dispersed in a mixture of 8 parts of ethylene glycol, 5 parts of Solbol AC3032 (trade mark, Toho Chemical Co., Ltd.), 0.1 part of xanthane gum and 56.9 parts of water. The thus-obtained mixture in the form of slurry was wet-pulverized by a Dino mill (produced by Symmal Enterprises Co.) to obtain a stable flowable agent containing 30% of an active ingredient.

TEST EXAMPLE 1

Treatment test on soil of flooded field

A plastic vat having an area of 1/2500 are was charged with the alluvial clay loam of paddy field, and the soil was fertilized and plowed while adding an appropriate amount of water thereto. On the thus-prepared soil, the seeds of barnyardgrass (Echinochloa crus-galli L. Beauv. var. crus-galli), toothcup (Rotala indica) and duck-tongue weed (Monochloria vaginalis) were sown. The seeds were mixed well with the soil in the layer within 0.5 cm of the surface.

2- to 3-leaf stage seedlings of rice plants (species: Akinishiki, quality of the seedlings: good) were transplanted to the vat in a depth of about 1 cm (3 roots per plant and 2 plants per vat). Thereafter, the water was maintained at a depth of 3.5 cm. 3 days after the transplantation, granules which contained a compound of the present invention as an active ingredient and which had been obtained in the same manner as in Formulation Example 2 were dropped to the flooded surfaces. For comparison, granules which contained a comparative compound as an active ingredient and which had been obtained in the same manner as in Formulation Example 2 were dropped to the flooded surfaces. The amounts of granules used were respectively so determined that the amounts of active ingredients contained were 10 g and 5 g, respectively, per are. After treating the soil with the granules, a leaching loss of water was adjusted at the rate of 3 cm/day for 2 days. Thereafter, the vats were kept in a greenhouse to allow growth of the plants under control. On the 21st day after the herbicidal treatment, the herbicidal effect and the phytotoxicity by the herbicide were examined.

The results are shown in Tables 10 to 12. The following equation was calculated and the evaluation of the herbicidal effect was represented by the herbicidal effect rate based on the following criteria:

$$\left[1 - \frac{\left(\begin{array}{c}\text{Survival terrestrial weeds} \\ \text{weight in treated area}\end{array}\right)}{\left(\begin{array}{c}\text{Survival terrestrial weeds} \\ \text{weight in non-treated area}\end{array}\right)}\right] \times 100 = Y(\%)$$

| Herbicidal effect rate | Y(%) |
|---|---|
| 0 | 0 to 5 |
| 1 | 6 to 30 |
| 2 | 31 to 50 |
| 3 | 51 to 70 |
| 4 | 71 to 90 |
| 5 | 91 to 100 |

The phytotoxicity by the herbicide to the paddyrice plants was evaluated by calculating the following formula and represented by the phytotoxicity rate based on the formula criteria:

$$\left[1 - \frac{\left(\begin{array}{c}\text{Survival terrestrial crop plant} \\ \text{weight in treated area}\end{array}\right)}{\left(\begin{array}{c}\text{Survival terrestrial crop plant} \\ \text{weight in non-treated area}\end{array}\right)}\right] \times 100 = Y'(\%)$$

| Phytotoxicity rate | Y'(%) |
|---|---|
| 0 | 0 to 5 |
| 1 | 6 to 10 |
| 2 | 11 to 20 |
| 3 | 21 to 40 |
| 4 | 41 to 60 |
| 5 | 61 to 100 |

TABLE 10

| Compound No | Dose g/are | Herbicidal effect rate Barnyard grass | Tooth cup | Duck-tongue weed | Phytotoxicity rate Rice |
|---|---|---|---|---|---|
| 1 | 10 | 3 | 5 | 5 | 0 |
|   | 5  | 2 | 3 | 3 | 0 |
| 2 | 10 | 3 | 5 | 5 | 0 |
|   | 5  | 2 | 3 | 3 | 0 |
| 3 | 10 | 4 | 5 | 5 | 0 |
|   | 5  | 3 | 5 | 5 | 0 |
| 4 | 10 | 4 | 5 | 5 | 0 |
|   | 5  | 3 | 5 | 5 | 0 |
| 5 | 10 | 3 | 5 | 5 | 0 |
|   | 5  | 2 | 4 | 4 | 0 |
| 6 | 10 | 3 | 5 | 5 | 0 |
|   | 5  | 2 | 3 | 3 | 0 |
| 7 | 10 | 3 | 5 | 5 | 0 |

TABLE 10-continued

| Compound No | Dose g/are | Barnyard grass | Tooth cup | Duck-tongue weed | Phytotoxicity rate Rice |
|---|---|---|---|---|---|
|  | 5 | 3 | 5 | 5 | 0 |
| 8 | 10 | 3 | 5 | 5 | 0 |
|  | 5 | 3 | 4 | 4 | 0 |
| 9 | 10 | 3 | 5 | 4 | 0 |
|  | 5 | 2 | 4 | 4 | 0 |
| 10 | 10 | 3 | 5 | 4 | 0 |
|  | 5 | 2 | 4 | 4 | 0 |
| 17 | 10 | 5 | 5 | 5 | 0 |
|  | 5 | 5 | 4 | 4 | 0 |
| 18 | 10 | 4 | 4 | 5 | 1 |
|  | 5 | 3 | 3 | 5 | 0 |
| 19 | 10 | 3 | 4 | 4 | 0 |
|  | 5 | 2 | 3 | 4 | 0 |
| 20 | 10 | 4 | 5 | 5 | 0 |
|  | 5 | 3 | 4 | 5 | 0 |
| 21 | 10 | 4 | 5 | 5 | 0 |
|  | 5 | 4 | 5 | 5 | 0 |
| 22 | 10 | 4 | 5 | 5 | 0 |
|  | 5 | 3 | 4 | 5 | 0 |
| 23 | 10 | 3 | 5 | 5 | 0 |
|  | 5 | 2 | 3 | 4 | 0 |
| 24 | 10 | 5 | 5 | 5 | 1 |
|  | 5 | 4 | 5 | 5 | 0 |
| 25 | 10 | 4 | 5 | 5 | 0 |
|  | 5 | 2 | 5 | 5 | 0 |
| 26 | 10 | 5 | 5 | 5 | 0 |
|  | 5 | 3 | 5 | 5 | 0 |
| 27 | 10 | 4 | 5 | 5 | 0 |
|  | 5 | 3 | 4 | 5 | 0 |
| 28 | 10 | 4 | 5 | 5 | 0 |
|  | 5 | 4 | 4 | 4 | 0 |
| 29 | 10 | 5 | 5 | 5 | 0 |
|  | 5 | 4 | 4 | 5 | 0 |
| 30 | 10 | 4 | 5 | 5 | 0 |
|  | 5 | 4 | 5 | 5 | 0 |
| 31 | 10 | 2 | 4 | 5 | 0 |
| 32 | 10 | 4 | 4 | 5 | 0 |
|  | 5 | 2 | 3 | 5 | 0 |
| 33 | 10 | 2 | 4 | 4 | 0 |
| 34 | 10 | 3 | 5 | 5 | 0 |
| 35 | 10 | 2 | 5 | 5 | 0 |
| 36 | 10 | 3 | 5 | 4 | 0 |
|  | 5 | 1 | 4 | 4 | 0 |
| 37 | 10 | 3 | 5 | 5 | 0 |
|  | 5 | 2 | 4 | 4 | 0 |
| 38 | 10 | 4 | 5 | 5 | 0 |
|  | 5 | 3 | 4 | 5 | 0 |
| 39 | 10 | 1 | 4 | 5 | 0 |
| Comparative compound | 10 | 3 | 1 | 3 | 3 |
|  | 5 | 2 | 0 | 2 | 0 |

(Note) Comparative compound: 1-(4-chlorophenoxy)phenyl-3,3-dimethylurea

TABLE 11

| Compound No | Dose g/are | Barnyard grass | Tooth cup | Duck-tongue weed | Phytotoxicity rate Rice |
|---|---|---|---|---|---|
| 40 | 10 | 3 | 4 | 5 | 0 |
|  | 5 | 1 | 4 | 3 | 0 |
| 43 | 10 | 3 | 5 | 5 | 1 |
|  | 5 | 3 | 5 | 4 | 0 |
| 44 | 10 | 3 | 5 | 5 | 0 |
|  | 5 | 2 | 5 | 4 | 0 |
| 45 | 10 | 3 | 5 | 5 | 0 |
|  | 5 | 3 | 4 | 5 | 0 |
| 47 | 10 | 3 | 5 | 5 | 0 |
|  | 5 | 0 | 5 | 4 | 0 |
| 48 | 10 | 2 | 4 | 5 | 0 |
|  | 5 | 1 | 4 | 3 | 0 |
| 49 | 10 | 2 | 5 | 5 | 1 |
|  | 5 | 0 | 5 | 5 | 0 |
| 50 | 10 | 3 | 5 | 5 | 0 |
|  | 5 | 2 | 4 | 4 | 0 |
| 52 | 10 | 3 | 5 | 5 | 0 |
|  | 5 | 0 | 4 | 4 | 0 |
| Comparative Compound | 10 | 1 | 4 | 4 | 2 |
|  | 5 | 0 | 4 | 3 | 1 |

(Note) Comparative compound: 1-4-[2-(40methylphenyl)ethyloxy]phenyl-3-methoxy-3-methylurea

TABLE 12

| Compound No. | Dose g/are | Barnyard grass | Tooth cup | Duck-tongue weed | Phytotoxicity rate Rice |
|---|---|---|---|---|---|
| 58 | 10 | 4 | 5 | 5 | 0 |
| 61 | 10 | 3 | 5 | 5 | 0 |
| 65 | 10 | 4 | 5 | 5 | 1 |
| 69 | 10 | 5 | 5 | 5 | 1 |
| 81 | 10 | 4 | 5 | 5 | 0 |
| 83 | 10 | 4 | 5 | 5 | 0 |
| 87 | 10 | 5 | 5 | 5 | 1 |
| 89 | 10 | 5 | 5 | 5 | 0 |
| 91 | 10 | 3 | 5 | 4 | 0 |
| 93 | 10 | 4 | 5 | 5 | 1 |
| 104 | 10 | 3 | 5 | 4 | 0 |
| 106 | 10 | 4 | 5 | 5 | 0 |
| 108 | 10 | 5 | 5 | 5 | 1 |
| 113 | 10 | 5 | 5 | 5 | 1 |
| Comparative Compound | 10 | 1 | 4 | 4 | 2 |

(Note) Comparative compound: 1-4-[2-(4-methylphenyl)-ethyloxy]phenyl-3-methoxy-3-methylurea

TEST EXAMPLE 2

Treatment test on foliage

A small-sized polyethylene pot having an area of 1/8850 are was charged with black volcano ash soil. After the soil was fertilized, the seeds of persicaria blumei gross (Polygonum blumei), lambsquarters (chenopodium album), velvetleaf (Abutilon theophtasti), deadnettle (Laminum amplexicaule), bed straw (Galium spurium), corn (Zea mays) and barley (Hordeum vulgare) were sown in the respective pots.

The pots were left in a greenhouse to allow growth of the plants under control. Wettable powders containing as an active ingredient a compound of the present invention and a comparative compound, obtained in the same way as in Formulation Example 1 were diluted with water so as to have a predetermined amount of active ingredient. When the test plants of persicaria blumei gross reached 2-leaf stage, lambsquarters reached 3-leaf stage, velvetleaf reached 2-leaf stage, dead-nettle reached 2-leaf stage, bedstraw reached 1.5-leaf stage, corn reached 3-leaf stage and barley reached 2-leaf stage, respectively, the wettable powders were sprayed by a smallsized power pressurized sprayer at a dosage of 10 litter per 1 are. Thereafter, the plants were observed in the greenhouse, and 15 days after the treatment, the herbicidal effect and the phytotoxicity of the crops from the compounds were examined. The results are shown in Table 13 to 16. The evaluation of the herbicidal effect and the phytotoxicity were based on the same criteria as in Test Example 1.

TABLE 13

| Compound No. | Dose g/are | Herbicidal effect rate | | | | | Phytotoxicity rate | |
|---|---|---|---|---|---|---|---|---|
| | | Persicaria blumei gross | Lambsquarters | Velvetleaf | Dead-nettle | Bedstraw | Corn | Barley |
| 1 | 10 | 5 | 5 | 3 | 5 | 5 | 0 | 0 |
|   | 5  | 2 | 2 | 1 | 2 | 2 | 0 | 0 |
| 2 | 10 | 5 | 5 | 3 | 5 | 4 | 0 | 0 |
|   | 5  | 2 | 2 | 1 | 3 | 2 | 0 | 0 |
| 3 | 10 | 5 | 5 | 5 | 5 | 5 | 1 | 1 |
|   | 5  | 4 | 3 | 2 | 3 | 3 | 1 | 0 |
| 4 | 10 | 5 | 5 | 5 | 5 | 5 | 1 | 1 |
|   | 5  | 4 | 3 | 2 | 2 | 3 | 1 | 0 |
|   | 5  | 4 | 3 | 2 | 2 | 3 | 1 | 0 |
| 5 | 10 | 5 | 5 | 3 | 5 | 5 | 1 | 1 |
| 6 | 10 | 5 | 5 | 3 | 5 | 5 | 1 | 1 |
| 7 | 10 | 5 | 5 | 5 | 5 | 5 | 1 | 1 |
|   | 5  | 4 | 3 | 2 | 3 | 3 | 0 | 0 |
| 8 | 10 | 5 | 5 | 5 | 5 | 5 | 1 | 1 |
|   | 5  | 4 | 3 | 2 | 3 | 3 | 0 | 0 |
| 9 | 10 | 5 | 5 | 4 | 5 | 5 | 0 | 0 |
| 10 | 10 | 5 | 5 | 4 | 5 | 5 | 0 | 0 |
| 11 | 10 | 5 | 5 | 3 | 5 | 4 | 0 | 0 |
| 12 | 10 | 5 | 5 | 3 | 5 | 4 | 0 | 0 |
| 13 | 10 | 5 | 5 | 3 | 5 | 4 | 0 | 0 |
|    | 5  | 2 | 2 | 2 | 3 | 2 | 0 | 0 |
| 14 | 10 | 5 | 5 | 3 | 5 | 4 | 0 | 0 |
|    | 5  | 2 | 2 | 2 | 3 | 2 | 0 | 0 |
| 15 | 10 | 5 | 5 | 3 | 5 | 4 | 0 | 0 |
| 16 | 10 | 5 | 5 | 3 | 5 | 4 | 0 | 0 |
| 17 | 10 | 5 | 5 | 5 | 5 | 5 | 1 | 0 |
|    | 5  | 4 | 4 | 5 | 3 | 3 | 0 | 0 |
| 18 | 10 | 4 | 4 | 5 | 3 | 4 | 0 | 0 |
| 19 | 10 | 4 | 4 | 3 | 4 | 3 | 0 | 0 |
| 20 | 10 | 5 | 5 | 5 | 5 | 5 | 1 | 2 |
|    | 5  | 5 | 5 | 5 | 5 | 4 | 0 | 0 |
| 21 | 10 | 5 | 5 | 5 | 5 | 5 | 0 | 1 |
|    | 5  | 5 | 5 | 5 | 4 | 4 | 0 | 0 |
| 22 | 10 | 5 | 5 | 5 | 5 | 5 | 0 | 1 |
|    | 5  | 4 | 4 | 5 | 3 | 3 | 0 | 0 |
| 23 | 10 | 4 | 4 | 4 | 3 | 3 | 0 | 0 |
| 24 | 10 | 5 | 5 | 5 | 5 | 5 | 1 | 1 |
|    | 5  | 5 | 5 | 5 | 4 | 4 | 0 | 0 |
| 25 | 10 | 5 | 5 | 5 | 5 | 5 | 0 | 0 |
|    | 5  | 4 | 5 | 5 | 4 | 3 | 0 | 0 |
| 26 | 10 | 5 | 5 | 5 | 5 | 5 | 0 | 0 |
|    | 5  | 4 | 5 | 5 | 4 | 4 | 0 | 0 |
| 27 | 10 | 5 | 5 | 5 | 5 | 5 | 0 | 1 |
|    | 5  | 4 | 5 | 5 | 3 | 4 | 0 | 0 |
| 28 | 10 | 5 | 5 | 5 | 5 | 5 | 0 | 0 |
|    | 5  | 4 | 5 | 5 | 4 | 4 | 0 | 0 |
| 29 | 10 | 4 | 5 | 5 | 5 | 5 | 0 | 0 |
|    | 5  | 4 | 4 | 5 | 4 | 3 | 0 | 0 |
| 30 | 10 | 4 | 3 | 5 | 3 | 2 | 0 | 0 |
| 31 | 10 | 5 | 5 | 5 | 5 | 5 | 0 | 0 |
|    | 5  | 5 | 5 | 4 | 5 | 4 | 0 | 0 |
| 32 | 10 | 5 | 4 | 5 | 5 | 4 | 1 | 2 |
|    | 5  | 5 | 3 | 5 | 3 | 3 | 0 | 0 |
| 33 | 10 | 5 | 4 | 5 | 5 | 5 | 0 | 0 |
|    | 5  | 5 | 4 | 4 | 4 | 2 | 0 | 0 |
| 34 | 10 | 4 | 4 | 3 | 3 | 2 | 0 | 0 |
| 35 | 10 | 5 | 5 | 5 | 5 | 5 | 0 | 1 |
|    | 5  | 5 | 5 | 5 | 5 | 5 | 0 | 0 |
| 36 | 10 | 3 | 3 | 4 | 3 | 2 | 0 | 0 |
| 37 | 10 | 4 | 5 | 3 | 2 | 2 | 0 | 0 |
| 38 | 10 | 5 | 5 | 5 | 5 | 5 | 0 | 0 |
|    | 5  | 4 | 3 | 5 | 3 | 3 | 0 | 0 |
| 39 | 10 | 4 | 3 | 3 | 2 | 2 | 0 | 0 |
| Comparative Compound | 10 | 4 | 4 | 2 | 4 | 2 | 2 | 3 |
|  | 5 | 2 | 1 | 1 | 3 | 0 | 1 | 2 |

(Note)
Comparative compound: 1-(4-chlorophenoxy)phenyl-3,3-dimethylurea

TABLE 14

| Compound No. | Dose g/are | Herbicidal effect rate | | | | | Phytotoxicity rate | |
|---|---|---|---|---|---|---|---|---|
| | | Persicaria blumei gross | Lambsquarters | Velvetleaf | Dead-nettle | Bedstraw | Corn | Barley |
| 40 | 10 | 5 | 4 | 4 | 5 | 4 | 0 | 1 |
| | 5 | 4 | 4 | 3 | 4 | 2 | 0 | 0 |
| 41 | 10 | 5 | 4 | 4 | 4 | 4 | 0 | 0 |
| | 5 | 3 | 4 | 4 | 3 | 3 | 0 | 0 |
| 42 | 10 | 5 | 5 | 4 | 5 | 4 | 0 | 1 |
| | 5 | 4 | 4 | 4 | 3 | 2 | 0 | 1 |
| 43 | 10 | 5 | 5 | 5 | 5 | 4 | 0 | 1 |
| | 5 | 5 | 4 | 4 | 5 | 3 | 0 | 1 |
| 44 | 10 | 5 | 5 | 5 | 5 | 4 | 0 | 1 |
| | 5 | 5 | 4 | 5 | 5 | 4 | 0 | 0 |
| 45 | 10 | 5 | 4 | 5 | 5 | 5 | 0 | 1 |
| | 5 | 5 | 3 | 5 | 4 | 3 | 0 | 1 |
| 46 | 10 | 5 | 5 | 4 | 4 | 4 | 0 | 1 |
| | 5 | 4 | 4 | 4 | 4 | 3 | 0 | 0 |
| 47 | 10 | 5 | 4 | 4 | 5 | 4 | 0 | 1 |
| | 5 | 5 | 3 | 3 | 4 | 3 | 0 | 0 |
| 48 | 10 | 5 | 4 | 4 | 4 | 4 | 0 | 0 |
| | 5 | 3 | 3 | 3 | 3 | 2 | 0 | 0 |
| 49 | 10 | 5 | 5 | 5 | 5 | 5 | 1 | 2 |
| | 5 | 5 | 5 | 5 | 4 | 4 | 0 | 0 |
| 50 | 10 | 10 | 5 | 5 | 5 | 4 | 1 | 1 |
| | 5 | 5 | 4 | 4 | 3 | 3 | 0 | 0 |
| 51 | 10 | 5 | 5 | 5 | 5 | 4 | 0 | 1 |
| | 5 | 5 | 3 | 4 | 4 | 3 | 0 | 0 |
| 52 | 10 | 5 | 4 | 5 | 5 | 5 | 0 | 1 |
| | 5 | 5 | 4 | 5 | 5 | 3 | 0 | 1 |
| 53 | 10 | 5 | 5 | 5 | 5 | 5 | 0 | 1 |
| | 5 | 5 | 4 | 5 | 4 | 4 | 0 | 0 |
| Comparative compound | 10 | 5 | 4 | 5 | 4 | 3 | 3 | 2 |
| | 5 | 3 | 3 | 4 | 3 | 1 | 2 | 1 |

(Note)
Comparative compound: 1-4-[2-(4-methylphenyl)ethyloxy]phenyl-3-methoxy-3-methylurea

TABLE 15

| Compound No. | Dose g/are | Herbicidal effect rate | | | | | Phytotoxicity rate | |
|---|---|---|---|---|---|---|---|---|
| | | *Persicaria blumei* gross | Lambsquarters | Velvetleaf | Dead-nettle | Bedstraw | Corn | Barley |
| 54 | 10 | 5 | 5 | 4 | 5 | 3 | 0 | 0 |
| 55 | 10 | 5 | 5 | 5 | 5 | 4 | 0 | 0 |
| | 5 | 5 | 4 | 4 | 5 | 3 | 0 | 0 |
| 56 | 10 | 5 | 5 | 5 | 5 | 5 | 2 | 0 |
| | 5 | 5 | 5 | 5 | 5 | 5 | 1 | 0 |
| 57 | 10 | 5 | 5 | 5 | 5 | 5 | 2 | 1 |
| | 5 | 4 | 5 | 4 | 5 | 4 | 1 | 0 |
| Comparative Compound A | 10 | 5 | 4 | 5 | 4 | 3 | 3 | 2 |
| | 5 | 3 | 3 | 4 | 3 | 1 | 2 | 1 |
| Comparative Compound B | 10 | 4 | 4 | 2 | 4 | 2 | 2 | 0 |
| | 5 | 2 | 1 | 1 | 3 | 0 | 1 | 2 |

(Note)
Comparative compound A: 1-4[2-(4-methylphenyl)ethyloxy]phenyl-3-methoxy-3-methylurea

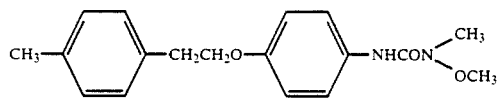

Comparative compound B: 1-(4-chlorophenoxy)phenyl-3,3-dimethylurea

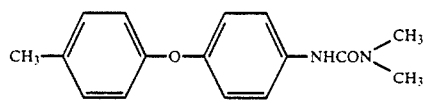

TABLE 16

| Compound No. | Dose g/are | Herbicidal effect rate | | | | | Phytotoxicity rate | |
|---|---|---|---|---|---|---|---|---|
| | | Persicaria blumei gross | Lambsquarters | Velvetleaf | Dead-nettle | Bedstraw | Corn | Barley |
| 58 | 10 | 4 | 5 | 4 | 5 | 4 | 0 | 0 |
| 59 | 10 | 4 | 5 | 4 | 4 | 4 | 0 | 0 |
| 60 | 10 | 5 | 5 | 4 | 5 | 4 | 0 | 0 |
| | 5 | 5 | 5 | 4 | 5 | 3 | 0 | 0 |
| 61 | 10 | 5 | 5 | 5 | 5 | 5 | 0 | 1 |
| | 5 | 5 | 5 | 3 | 5 | 4 | 0 | 0 |
| 62 | 10 | 5 | 5 | 5 | 5 | 5 | 1 | 1 |
| 63 | 10 | 5 | 5 | 5 | 5 | 5 | 1 | 2 |
| | 5 | 5 | 5 | 4 | 5 | 3 | 0 | 1 |
| 64 | 10 | 4 | 5 | 4 | 5 | 5 | 0 | 0 |
| 65 | 10 | 4 | 5 | 5 | 5 | 5 | 0 | 0 |
| 66 | 10 | 5 | 5 | 5 | 5 | 4 | 0 | 0 |
| | 5 | 5 | 5 | 4 | 5 | 4 | 0 | 0 |
| 67 | 10 | 5 | 5 | 5 | 5 | 4 | 0 | 0 |
| 68 | 10 | 5 | 5 | 4 | 5 | 4 | 0 | 0 |
| 69 | 10 | 4 | 4 | 3 | 5 | 3 | 0 | 0 |
| 70 | 10 | 4 | 4 | 4 | 4 | 3 | 0 | 0 |
| 71 | 10 | 4 | 5 | 4 | 4 | 4 | 0 | 0 |
| 72 | 10 | 5 | 5 | 4 | 5 | 5 | 0 | 0 |
| 73 | 10 | 5 | 5 | 4 | 5 | 5 | 0 | 1 |
| | 5 | 5 | 4 | 4 | 5 | 4 | 0 | 0 |
| 74 | 10 | 4 | 5 | 4 | 5 | 4 | 0 | 0 |
| 75 | 10 | 5 | 5 | 4 | 5 | 4 | 0 | 0 |
| 76 | 10 | 4 | 5 | 4 | 5 | 4 | 0 | 0 |
| 77 | 10 | 4 | 5 | 5 | 4 | 5 | 0 | 0 |
| 78 | 10 | 4 | 5 | 5 | 5 | 5 | 0 | 0 |
| 79 | 10 | 5 | 4 | 4 | 5 | 5 | 0 | 0 |
| 80 | 10 | 5 | 5 | 4 | 5 | 5 | 0 | 0 |
| 81 | 10 | 4 | 5 | 5 | 5 | 4 | 0 | 0 |
| 82 | 10 | 4 | 4 | 4 | 5 | 3 | 0 | 0 |
| 83 | 10 | 5 | 5 | 5 | 5 | 5 | 1 | 1 |
| | 5 | 5 | 5 | 3 | 5 | 4 | 0 | 0 |
| 84 | 10 | 5 | 5 | 5 | 5 | 5 | 1 | 0 |
| | 5 | 5 | 5 | 4 | 5 | 4 | 0 | 0 |
| 85 | 10 | 5 | 5 | 5 | 5 | 5 | 1 | 1 |
| | 5 | 5 | 5 | 4 | 5 | 5 | 0 | 1 |
| 86 | 10 | 5 | 5 | 5 | 5 | 5 | 0 | 1 |
| | 5 | 5 | 5 | 5 | 5 | 4 | 0 | 0 |
| 87 | 10 | 5 | 5 | 4 | 5 | 4 | 0 | 0 |
| 88 | 10 | 4 | 5 | 4 | 5 | 3 | 0 | 0 |
| 89 | 10 | 5 | 5 | 5 | 5 | 5 | 0 | 0 |
| | 5 | 5 | 5 | 4 | 5 | 5 | 0 | 0 |
| 90 | 10 | 5 | 5 | 4 | 5 | 4 | 0 | 0 |
| 91 | 10 | 4 | 4 | 3 | 5 | 4 | 0 | 0 |
| 92 | 10 | 4 | 4 | 3 | 4 | 4 | 0 | 0 |
| 93 | 10 | 5 | 5 | 5 | 5 | 5 | 1 | 2 |
| | 5 | 5 | 5 | 5 | 5 | 5 | 0 | 1 |
| 94 | 10 | 5 | 5 | 4 | 5 | 3 | 0 | 0 |
| 95 | 10 | 4 | 5 | 4 | 5 | 3 | 0 | 0 |
| 96 | 10 | 4 | 5 | 4 | 5 | 4 | 0 | 0 |
| 97 | 10 | 5 | 4 | 3 | 5 | 4 | 0 | 0 |
| 98 | 10 | 5 | 4 | 4 | 5 | 3 | 0 | 0 |
| 99 | 10 | 4 | 5 | 4 | 5 | 4 | 0 | 0 |
| 100 | 10 | 5 | 5 | 3 | 5 | 4 | 0 | 0 |
| 101 | 10 | 5 | 4 | 4 | 4 | 4 | 0 | 0 |
| 102 | 10 | 5 | 5 | 4 | 5 | 4 | 0 | 0 |
| 103 | 10 | 5 | 5 | 5 | 5 | 5 | 0 | 0 |
| | 5 | 5 | 5 | 4 | 5 | 5 | 0 | 0 |
| 104 | 10 | 5 | 5 | 4 | 5 | 5 | 0 | 0 |
| 105 | 10 | 5 | 5 | 4 | 5 | 4 | 0 | 0 |
| 106 | 10 | 5 | 5 | 3 | 5 | 3 | 0 | 0 |
| 107 | 10 | 5 | 4 | 4 | 5 | 3 | 0 | 0 |
| 108 | 10 | 5 | 5 | 5 | 5 | 5 | 1 | 1 |
| | 5 | 5 | 5 | 5 | 5 | 5 | 0 | 0 |
| 109 | 10 | 5 | 5 | 5 | 5 | 5 | 0 | 0 |
| 110 | 10 | 5 | 5 | 4 | 5 | 5 | 0 | 0 |
| | 5 | 5 | 5 | 4 | 5 | 4 | 0 | 0 |
| 111 | 10 | 5 | 5 | 5 | 5 | 5 | 1 | 2 |
| | 5 | 5 | 5 | 4 | 5 | 5 | 0 | 1 |
| 112 | 10 | 4 | 4 | 3 | 5 | 3 | 0 | 0 |
| 113 | 10 | 5 | 5 | 4 | 5 | 5 | 0 | 0 |
| | 5 | 5 | 5 | 4 | 5 | 3 | 0 | 0 |
| 114 | 10 | 5 | 5 | 4 | 5 | 4 | 0 | 0 |
| Comparative Com- | 10 | 4 | 4 | 4 | 4 | 3 | 3 | 2 |
| | 5 | 3 | 3 | 2 | 3 | 1 | 2 | 1 |

TABLE 16-continued

| Compound No. | Dose g/are | Herbicidal effect rate | | | | | Phytotoxicity rate | |
|---|---|---|---|---|---|---|---|---|
| | | *Persicaria blumei gross* | Lambsquarters | Velvetleaf | Deadnettle | Bedstraw | Corn | Barley |
| pound | | | | | | | | |

(Note)
Comparative compound: 1-4-[2-(4-methylphenyl)ethyloxy]phenyl-3-methoxy-3-methylurea

What is claimed is:

1. A compound represented by the following general formula (I):

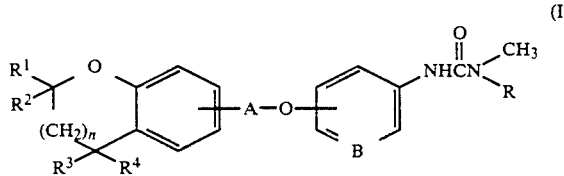

wherein A represents an ethylene group or an isopropylene group; B represents a nitrogen atom or CH; R represents a hydrogen atom, a lower alkyl group or a lower alkoxy group; $R^1$, $R^2$, $R^3$ and $R^4$ independently represent a hydrogen atom or a methyl group; and n is 0 or 1.

2. A compound according to claim 1, wherein said compound is an N'-aryl-N-methylurea derivative represented by the following general formula (II):

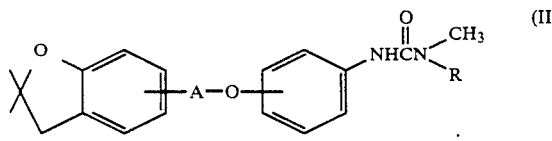

wherein A represents an ethylene group or an isopropylene group; and R represents a hydrogen atom, a lower alkyl group or a lower alkoxy group.

3. A compound according to claim 1, wherein said compound is an N'-phenyl-N-methylurea derivative represented by the following general formula (III):

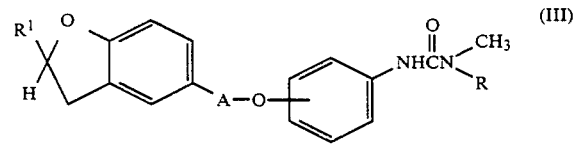

wherein A represents an ethylene group or an isopropylene group; R represents a hydrogen atom, a lower alkyl group or a lower alkoxy group. group; and $R^1$ represents a hydrogen atom or a methyl 4. A compound according to claim 1, wherein said compound is an N'-(5-pyridyl)-N-methylurea derivative represented by the following general formula (IV):

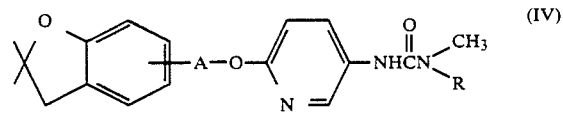

wherein A represents an ethylene group or an isopropylene group; and R represents a hydrogen atom, a lower alkyl group or a lower alkoxy group.

5. A compound according to claim 1, wherein said compound is an N'-phenyl-N-methylurea derivative represented by the following general formula (V):

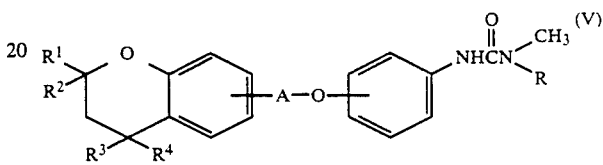

wherein A represents an ethylene group or an isopropylene group; R represents a hydrogen atom, a lower alkyl group or a lower alkoxy group; and $R^1$, $R^2$, $R^3$ and $R^4$ independantly represent a hydrogen atom or a methyl group.

6. A compound according to claim 2, wherein A represents an ethylene group or an isopropylene group; and R represents a methyl group or a methoxy group.

7. A compound according to claim 3, wherein A represents an ethylene group or an isopropylene group; R represents a methyl group or a methoxy group; and $R^1$ represents a methyl group.

8. A compound according to claim 5, wherein A represents an ethylene group or an isopropylene group; R represents a methyl group or a methoxy group; $R^1$ and $R^2$ respectively represent a hydrogen atom or a methyl group; and $R^3$ and $R^4$ respectively represent a hydrogen atom.

9. A herbicidal composition comprising as an active ingredient a herbicidally effective amount of compound represented by the following general formula:

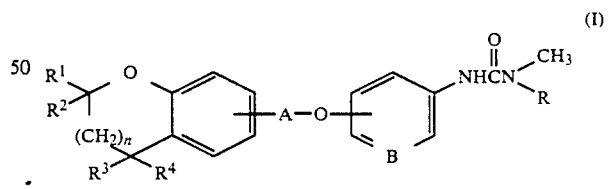

wherein A represents an ethylene group or an isopropylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1, and
a herbicidally acceptable carrier or adjuvant.

10. A compound according to claim 1, wherein B is CH.

11. A herbicidal composition according to claim 9, wherein said compound is an N'-aryl-N-methylurea derivative represented by the following general formula (II):

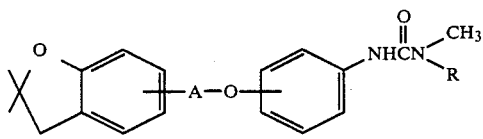

wherein A represents an ethylene group or an isopropylene group; and R represents a hydrogen atom, a lower alkyl group or a lower alkoxy group.

12. A herbicidal composition according to claim 9, wherein said compound is an N'-phenyl-N-methylurea derivative represented by the following general formula (III):

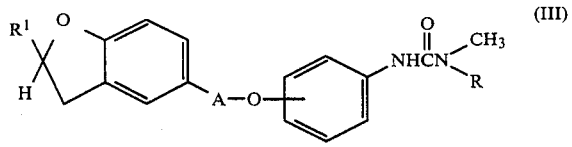

wherein A represents an ethylene group or an isopropylene group; R represents a hydrogen atom, a lower alkyl group or a lower alkoxy group; and $R^1$ represents a hydrogen atom or a methyl group.

13. A herbicidal composition according to claim 9, wherein said compound is an N'-(5-pyridyl)-N-methylurea derivative represented by the following general formula (IV):

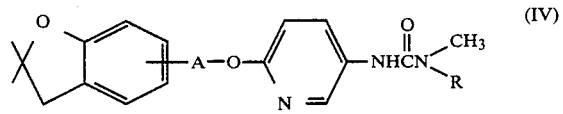

wherein A represents an ethylene group or an isopropylene group; and R represents a hydrogen atom, a lower alkyl group or a lower alkoxy group.

14. A herbicidal composition according to claim 9, wherein said compound is an N'-phenyl-N-methylurea derivative represented by the following general formula (V):

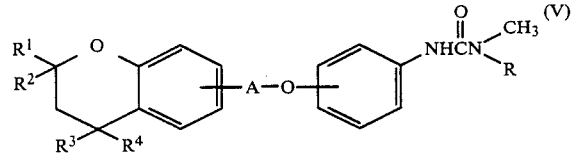

wherein A represents an ethylene group or an isopropylene group; R represents a hydrogen atom, a lower alkyl group or a lower alkoxy group; and $R^1$, $R^2$, $R^3$ and $R^4$, independantly represent a hydrogen atom or a methyl group.

15. A herbicidal composition according to claim 11, wherein A represents an ethylene group or an isopropyl group; and R represents a methyl group or a methoxy group.

16. A herbicidal composition according to claim 12, wherein A represents an ethylene group or an isopropylene group; R represents a methyl group or a methoxy group; and $R^1$ represents a methyl group.

17. A herbicidal composition according to claim 14, wherein A represents an ethylene group or an isopropylene group; R represents a methyl group or a methoxy group; $R^1$ and $R^2$ respectively represent a hydrogen atom or a methyl group; and $R^3$ and $R^4$ respectively represent a hydrogen atom.

18. A herbicidal composition according to claim 9, wherein B is CH.

19. A method of controlling the growth of weeds, which method comprises applying a herbicidally effective amount of compound represented by the following general formula:

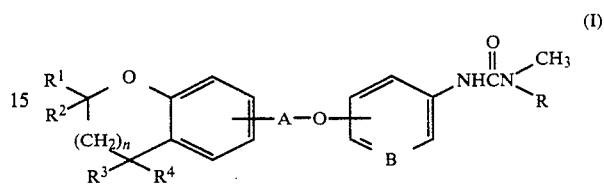

wherein A represents an ethylene group or an isopropylene group; B represents a nitrogen atom or CH; R represents a hydrogen atom, a lower alkyl group or a lower alkoxy group; $R^1$, $R^2$, $R^3$ and $R^4$ independantly represent a hydrogen atom or a methyl group; and n is 0 or 1.

20. A method according to claim 19, wherein said compound is an N'-aryl-N-methylurea derivative represented by the following general formula (II):

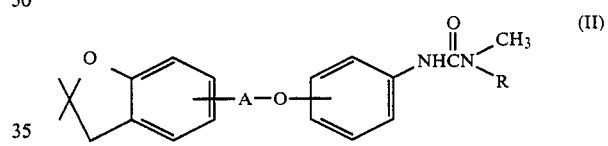

wherein A represents an ethylene group or an isopropylene group; and R represents a hydrogen atom, a lower alkyl group or a lower alkoxy group.

21. A method according to claim 19, wherein said compound is an N'-phenyl-N-methylurea derivative represented by the following general formula (III):

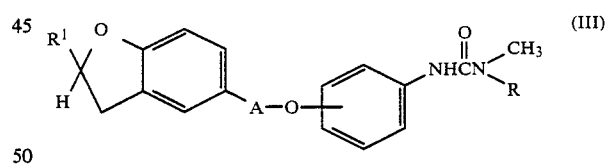

wherein A represents an ethylene group or an isopropylene group; R represents a hydrogen atom, a lower alkyl group or a lower alkoxy group; and $R^1$ represents a hydrogen atom or a methyl group.

22. A method according to claim 19, wherein said compound is an N'-(5-pyridyl)-N-methylurea derivative represented by the following general formula (IV):

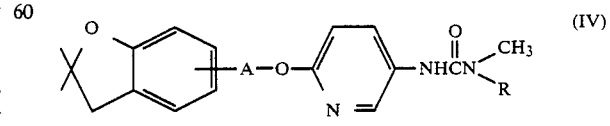

wherein A represents an ethylene group or an isopropylene group; and R represents a hydrogen atom, a lower alkyl group or a lower alkoxy group.

23. A method according to claim 19, wherein said compound is an N'-phenyl-N-methylurea derivative represented by the following general formula (V):

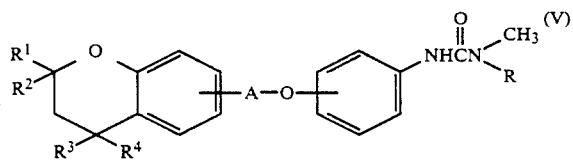

wherein A represents an ethylene group or an isopropylene group; R represents a hydrogen atom, a lower alkyl group or a lower alkoxy group; and $R^1$, $R^2$, $R^3$ and $R^4$ independantly represent a hydrogen atom or a methyl group.

24. A method according to claim 20, wherein A represents an ethylene group or an isopropylene group; and R represents a methyl group or a methoxy group.

25. A method according to claim 21, wherein A represents an ethylene group or an isopropyl group; R represents a methyl group or a methoxy group; and $R^1$ represents a methyl group.

26. A method according to claim 23, wherein A represents an ethylene group or an isopropylene group; R represents a methyl group or a methoxy group; $R^1$ and $R^2$ respectively represent a hydrogen atom or a methyl group; and $R^3$ and $R^4$ respectively represent a hydrogen atom.

27. A method according to claim 19, wherein B in the compound of formula (I) is CH.

* * * * *

UNITED STATES PATENT AND TRADEMARK OFFICE
CERTIFICATE OF CORRECTION

PATENT NO. : 4,959,092
DATED : SEPTEMBER 25, 1990
INVENTOR(S) : HIROKI OHTA ET AL.

It is certified that error appears in the above-identified patent and that said Letters Patent is hereby corrected as shown below:

On the title page, item [30]:
In the Foreign Application Priority Data, please delete the last Serial Number "63-315860" and insert --62-315860--.

Signed and Sealed this

Twenty-first Day of January, 1992

Attest:

HARRY F. MANBECK, JR.

*Attesting Officer*      *Commissioner of Patents and Trademarks*